(12) United States Patent
Levade et al.

(10) Patent No.: US 10,822,415 B2
(45) Date of Patent: Nov. 3, 2020

(54) METHODS FOR ENHANCING THE POTENCY OF THE IMMUNE CHECKPOINT INHIBITORS

(71) Applicants: INSERM (INSTITUT NATIONAL DE LA SANTÉ ET DE LA RECHERCHE MÉDICALE), Paris (FR); Université Toulouse III—Paul Sabatier, Toulouse (FR); CENTRE HOSPITALIER UNIVERSITAIRE DE TOULOUSE, Toulouse (FR)

(72) Inventors: Thierry Levade, Toulouse (FR); Nicolas Meyer, Toulouse (FR); Céline Colacios Viatgé, Toulouse (FR); Caroline Imbert, Toulouse (FR); Nathalie Andrieu-Abadie, Toulouse (FR); Bruno Segui, Toulouse (FR)

(73) Assignees: INSERM (INSTITUT NATIONAL DE LA SANTÉET DE LA RECHERCHE MÉDICALE), Paris (FR); Université Toulouse III—Paul Sabatier, Toulouse (FR); CENTRE HOSPITALIER UNIVERSITAIRE DE TOULOUSE, Toulouse (FR)

( * ) Notice: Subject to any disclaimer, the term of this patent is extended or adjusted under 35 U.S.C. 154(b) by 41 days.

(21) Appl. No.: 16/073,080

(22) PCT Filed: Jan. 27, 2017

(86) PCT No.: PCT/EP2017/051812
§ 371 (c)(1),
(2) Date: Jul. 26, 2018

(87) PCT Pub. No.: WO2017/129769
PCT Pub. Date: Aug. 3, 2017

(65) Prior Publication Data
US 2019/0031757 A1    Jan. 31, 2019

(30) Foreign Application Priority Data
Jan. 28, 2016    (EP) .................................... 16305084

(51) Int. Cl.
| | |
|---|---|
| A61K 39/00 | (2006.01) |
| C07K 16/28 | (2006.01) |
| A61K 31/133 | (2006.01) |
| A61K 31/137 | (2006.01) |
| A61K 31/40 | (2006.01) |
| A61K 31/415 | (2006.01) |
| A61K 31/4245 | (2006.01) |
| A61K 31/426 | (2006.01) |
| A61K 31/4535 | (2006.01) |
| A61K 45/06 | (2006.01) |
| A61K 39/395 | (2006.01) |
| G01N 33/569 | (2006.01) |
| A61P 35/00 | (2006.01) |
| G01N 33/574 | (2006.01) |

(52) U.S. Cl.
CPC ........ *C07K 16/2818* (2013.01); *A61K 31/133* (2013.01); *A61K 31/137* (2013.01); *A61K 31/40* (2013.01); *A61K 31/415* (2013.01); *A61K 31/426* (2013.01); *A61K 31/4245* (2013.01); *A61K 31/4535* (2013.01); *A61K 39/3955* (2013.01); *A61K 45/06* (2013.01); *A61P 35/00* (2018.01); *G01N 33/56972* (2013.01); *G01N 33/574* (2013.01); *A61K 2039/505* (2013.01); *A61K 2039/507* (2013.01); *G01N 2333/70517* (2013.01); *G01N 2800/52* (2013.01)

(58) Field of Classification Search
CPC .................................................. C07K 16/2818
See application file for complete search history.

(56) References Cited

U.S. PATENT DOCUMENTS

| | | | | |
|---|---|---|---|---|
| 8,372,888 B2 * | 2/2013 | Zipkin | ...................... | A61P 7/08 514/653 |
| 2007/0048803 A1 * | 3/2007 | Lee | ...................... | G01N 33/505 435/7.2 |
| 2012/0329878 A1 * | 12/2012 | Coussens | ................ | A61P 35/00 514/651 |
| 2013/0164762 A1 * | 6/2013 | Emile | ................... | G06T 7/0012 435/7.23 |
| 2015/0210769 A1 * | 7/2015 | Freeman | .............. | G01N 33/566 424/136.1 |

OTHER PUBLICATIONS

Imbert, Nature Communications (2020) 14 pages (Year: 2020).*
Kim Teresa et al: "Combining targeted therapy and immune checkpoint inhibitors in the treatment of metastatic meloma." Cancer Biology & Medicine Dec. 2014, vol. 11, No. 4, Dec. 2014, pp. 237-246.

(Continued)

*Primary Examiner* — Sheela J. Huff
(74) *Attorney, Agent, or Firm* — W&C IP

(57) ABSTRACT

The present invention relates to methods for enhancing the potency of the immune checkpoint inhibitors. In particular, the present invention relates to a method for enhancing the potency of an immune checkpoint inhibitor administered to a subject as part of a treatment regimen, the method comprising administering a pharmaceutically effective amount of a SK1 inhibitor to a subject in combination with the immune checkpoint inhibitor.

7 Claims, 9 Drawing Sheets

(56) References Cited

OTHER PUBLICATIONS

Figure 1:
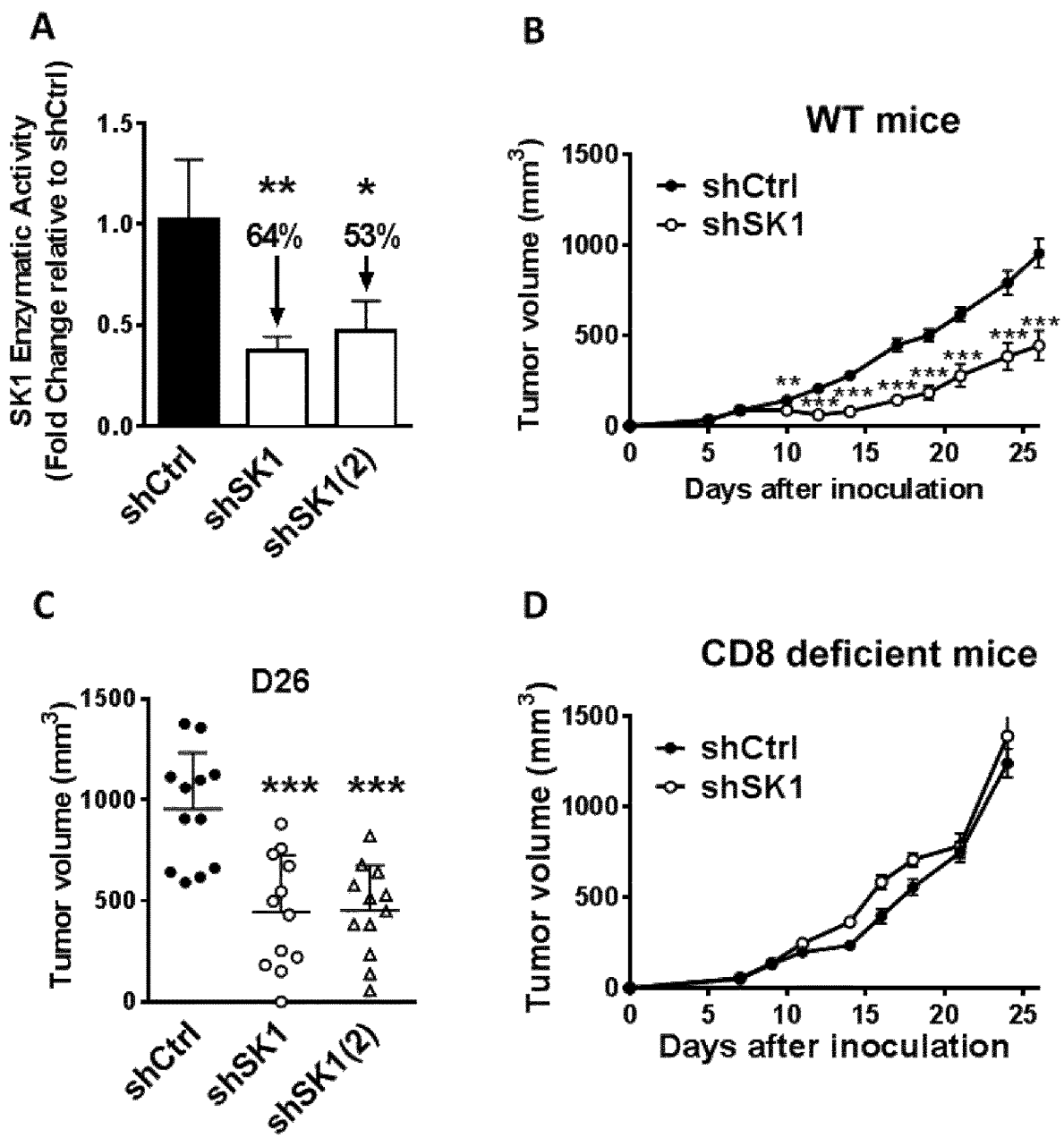

Madhunapantula Subbarao V et al: "Targetting sphingosine kinase-1 to inhibit melanoma", Pigment Cell & Melanoma Research, vol. 25, No. 2, Mar. 2012, p. 261; col. 2, p. 268, col. 1-col. 2.

Neeraj N. Patwardhan et al: "Structure-Activity Relationship Studies and in Vivo Activity of Guanidine-Based Sphingosine Kinase Inhibitors: Discovery of SphK1- and SphK2-Selective Inhibitors", Journal of Medicinal Chemistry, vol. 58, No. 4, Feb. 26, 2015, pp. 1879-1899.

* cited by examiner

A

B

A

B

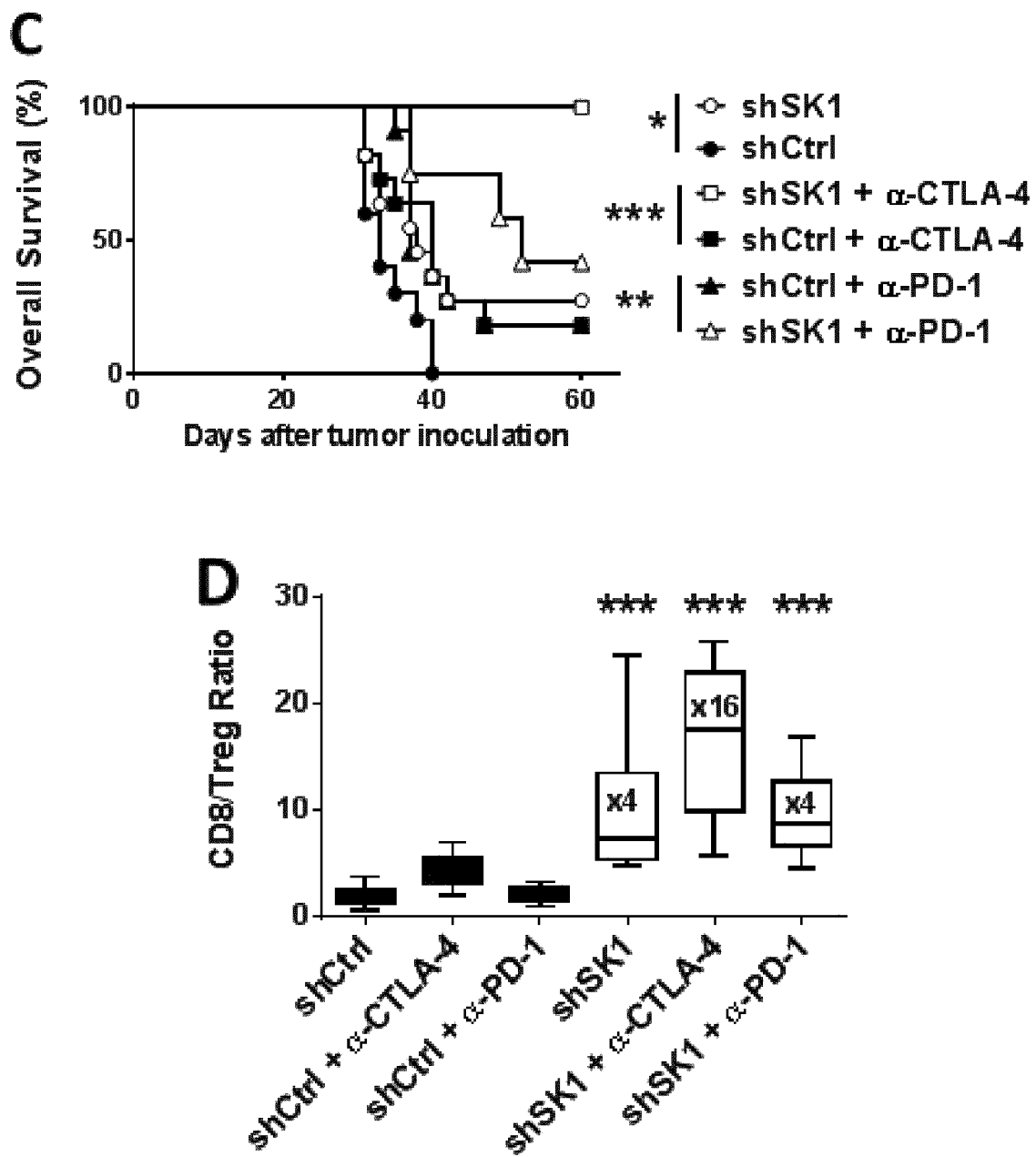
Figure 3 C and D

A

B

A

B

METHODS FOR ENHANCING THE POTENCY OF THE IMMUNE CHECKPOINT INHIBITORS

FIELD OF THE INVENTION

The present invention relates to methods for enhancing the potency of the immune checkpoint inhibitors.

BACKGROUND OF THE INVENTION

The ability of the immune system to detect and eliminate cancer was first proposed over 100 years ago. Since then, T cells reactive against tumor-associated antigens have been detected in the blood of patients with many different types of cancers, suggesting a role for the immune system in fighting cancer. However, tumors can escape host immunity by manipulating the tumor microenvironment and driving immunosuppression, meaning that patients cannot mount a potent enough immune response to fully eliminate cancer cells. The goal of immunotherapy is to restore or augment antitumor immune responses. An increased understanding of tumor immunology has led to the identification of novel targets for new immune-based approaches, including a group of cell-surface molecules known as immune checkpoint proteins. In particular, monoclonal antibodies inhibiting CTLA-4 (ipilimumab) or PD-1 (nivolumab, pembrolizumab) have demonstrated significant efficacy in the treatment of metastatic melanoma, promoting high response rate and long-lasting tumor control. Despite promising results, about 40% of patients do not display therapeutic response and a significant proportion of responders experience tumor relapse in the 2 years following treatment induction. Moreover, recent clinical trials combining BRAF and checkpoint inhibitors have shown high liver toxicity for patients with BRAF-mutated melanoma. Accordingly, development of novel therapeutic strategies is thus urgently needed in order to enhance the potency of the immune checkpoint inhibitor.

Sphingolipid metabolites, including ceramide, ceramide 1-phosphate, sphingosine, and sphingosine 1-phosphate (S1P), have emerged as bioactive signalling molecules that regulate cell motility, differentiation, proliferation and survival as well as angiogenesis, inflammation and immunity. It was recently demonstrated an increased production of S1P in melanoma cells (2, 3). This bioactive sphingolipid metabolite is produced mainly by sphingosine kinase 1 (SK1), which is overexpressed in human melanoma tumors compared to nevi (2). In many tumors, S1P conveys oncogenic signals as an intracellular second messenger and/or through the stimulation of a family of G-protein coupled receptors (S1PR1-5) expressed both on cancer cells and their surrounding microenvironment (4, 5). In melanoma tumors, dysregulation of S1P production in cancer cells elicits a fibrotic response in the tumor microenvironment, which in turn stimulates melanoma cell migration (2). Additionally, treatment of mice with the S1P receptor modulator FTY720, which renders cells unresponsive to S1P activation by sequestering S1PR1 internally, reduced melanoma progression by inhibiting tumor vascularization (6). These findings illustrate the paracrine action of melanoma cell-exported S1P through S1PRs on tumor-stroma interactions. However, recent studies demonstrate that the SK1/S1P/S1PR axis plays an essential role in inflammation-associated cancer development (7). Indeed, shRNA-based downregulation of SK1 or S1PR1 has been shown to block the persistent activation of the transcription factor STAT3 and the level of proinflammatory cytokines and reduce cancer progression in mouse models of inflammation (8, 9). In addition, S1P contributes to trafficking and effector functions of lymphocytes and other hematopoietic cells (10). However, the prior art does not suggest SK1 inhibition could enhance the potency of the immune checkpoint inhibitors.

SUMMARY OF THE INVENTION

The present invention relates to methods for enhancing the potency of the immune checkpoint inhibitors. In particular, the present invention is defined by the claims.

DETAILED DESCRIPTION OF THE INVENTION

The inventors demonstrated that interfering with sphingolipid metabolism efficiently impairs tumor progression in pre-clinical melanoma model and enhances anti-tumor immune response obtained with the immune checkpoint inhibitor. In particular, the inventors observed that SK1 downregulation enhances proliferation and activation of CD8+ T cells within the tumors. Of great interest is the finding that SK1 knockdown in melanoma enhances the expression of CTLA-4 and PD-1 on CD8+ TIL, which are both up-regulated upon T cell activation and exert potent negative feedback loop on T cell activation. The latter observation highlights for the first time that melanoma SK1 impairs CD8+ T cell-dependent immune response. However, the upregulation of both PD-1 and CTLA-4 on CD8+ T cells is likely involved in the melanoma immune escape following SK1 knockdown observed at latter time points. Thus, targeting melanoma SK1 is unlikely sufficient to trigger total tumor regression. Collectively, the data prompted the inventors to investigate the combination of SK1 inhibition with the inhibition of immune checkpoints and demonstrate that said combination provides synergistic anti-cancer immune responses.

Accordingly the first object of the present invention relates to a method of enhancing the proliferation and activation of tumor infiltrating CD8+ T cells in a patient suffering from cancer comprising administering to the patient a therapeutically effective amount of a SK1 inhibitor.

As used herein, the term "CD8+ T cell" has its general meaning in the art and refers to a subset of T cells which express CD8 on their surface. They are MHC class I-restricted, and function as cytotoxic T cells. "CD8+ T cells" are also called cytotoxic T lymphocytes (CTL), T-killer cells, cytolytic T cells, or killer T cells. CD8 antigens are members of the immunoglobulin supergene family and are associative recognition elements in major histocompatibility complex class I-restricted interactions. As used herein, the term "tumor infiltrating CD8+ T cell" refers to the pool of CD8+ T cells of the patient that have left the blood stream and have migrated into a tumor.

A further object of the present invention relates to a method for enhancing the potency of an immune checkpoint inhibitor administered to a subject as part of a treatment regimen, the method comprising administering to the subject a pharmaceutically effective amount of a SK1 inhibitor in combination with the immune checkpoint inhibitor.

As used herein the term "immune checkpoint protein" has its general meaning in the art and refers to a molecule that is expressed by T cells in that either turn up a signal (stimulatory checkpoint molecules) or turn down a signal (inhibitory checkpoint molecules). Immune checkpoint molecules are recognized in the art to constitute immune checkpoint pathways similar to the CTLA-4 and PD-1 dependent pathways (see e.g. Pardoll, 2012. Nature Rev Cancer 12:252-264; Mellman et al., 2011. Nature 480:480-489). Examples of inhibitory checkpoint molecules include A2AR, B7-H3, B7-H4, BTLA, CTLA-4, CD277, IDO, KIR, PD-1, LAG-3, TIM-3 and VISTA. The Adenosine A2A receptor (A2AR) is regarded as an important checkpoint in cancer therapy because the tumor microenvironment has relatively high levels of adenosine, which lead to a negative immune feedback loop through the activation of A2AR. B7-H3, also called CD276, was originally understood to be a co-stimulatory molecule but is now regarded as co-inhibitory. B7-H4, also called VTCN1, is expressed by tumor cells and tumor-associated macrophages and plays a role in tumor escape. B and T Lymphocyte Attenuator (BTLA), also called CD272, is a ligand of HVEM (Herpesvirus Entry Mediator). Cell surface expression of BTLA is gradually downregulated during differentiation of human CD8+ T cells from the naive to effector cell phenotype, however tumor-specific human CD8+ T cells express high levels of BTLA. CTLA-4, Cytotoxic T-Lymphocyte-Associated protein 4 and also called CD152 is overexpressed on Treg cells serves to control T cell proliferation. IDO, Indoleamine 2,3-dioxygenase, is a tryptophan catabolic enzyme, a related immune-inhibitory enzymes. Another important molecule is TDO, tryptophan 2,3-dioxygenase. IDO is known to suppress T and NK cells, generate and activate Tregs and myeloid-derived suppressor cells, and promote tumor angiogenesis. KIR, Killer-cell Immunoglobulin-like Receptor, is a receptor for MHC Class I molecules on Natural Killer cells. LAG3, Lymphocyte Activation Gene-3, works to suppress an immune response by action to Tregs as well as direct effects on CD8+ T cells. PD-1, Programmed Death 1 (PD-1) receptor, has two ligands, PD-L1 and PD-L2. This checkpoint is the target of Merck & Co.'s melanoma drug Keytruda, which gained FDA approval in September 2014. An advantage of targeting PD-1 is that it can restore immune function in the tumor microenvironment. TIM-3, short for T-cell Immunoglobulin domain and Mucin domain 3, expresses on activated human CD4+ T cells and regulates Th1 and Th17 cytokines. TIM-3 acts as a negative regulator of Th1/Tc1 function by triggering cell death upon interaction with its ligand, galectin-9. VISTA. Short for V-domain Ig suppressor of T cell activation, VISTA is primarily expressed on hematopoietic cells so that consistent expression of VISTA on leukocytes within tumors may allow VISTA blockade to be effective across a broad range of solid tumors.

As used herein, the term "immune checkpoint inhibitor" has its general meaning in the art and refers to any compound inhibiting the function of an immune inhibitory checkpoint protein. Inhibition includes reduction of function and full blockade. Preferred immune checkpoint inhibitors are antibodies that specifically recognize immune checkpoint proteins. A number of immune checkpoint inhibitors are known and in analogy of these known immune checkpoint protein inhibitors, alternative immune checkpoint inhibitors may be developed in the (near) future. The immune checkpoint inhibitors include peptides, antibodies, nucleic acid molecules and small molecules. In particular, the immune checkpoint inhibitor of the present invention is administered for enhancing the proliferation, migration, persistence and/or cytoxic activity of CD8+ T cells in the subject and in particular the tumor-infiltrating of CD8+ T cells of the subject.

Thus the expression "enhancing the potency of an immune checkpoint" refers to the ability of the SK1 inhibitor to increase the ability of the immune checkpoint inhibitor to enhance the proliferation, migration, persistence and/or cytoxic activity of CD8+ T cells.

As used herein, the term "treatment" or "treat" refer to both prophylactic or preventive treatment as well as curative or disease modifying treatment, including treatment of patient at risk of contracting the disease or suspected to have contracted the disease as well as patients who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a patient during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a patient during treatment of an illness, e.g., to keep the patient in remission for long periods of time (months or years). A maintenance regimen may employ continuous therapy (e.g., administering a drug at a regular intervals, e.g., weekly, monthly, yearly, etc.) or intermittent therapy (e.g., interrupted treatment, intermittent treatment, treatment at relapse, or treatment upon achievement of a particular predetermined criteria [e.g., pain, disease manifestation, etc.]).

In some embodiments, the subject suffers from a cancer. As used herein, the term "cancer" has its general meaning in the art and includes, but is not limited to, solid tumors and blood-borne tumors. The term cancer includes diseases of the skin, tissues, organs, bone, cartilage, blood and vessels. The term "cancer" further encompasses both primary and metastatic cancers. Examples of cancers that may be treated by methods and compositions of the invention include, but are not limited to, cancer cells from the bladder, blood, bone, bone marrow, brain, breast, colon, esophagus, gastrointestinal tract, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous; adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; Paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; and roblastoma, malignant; Sertoli cell carcinoma; Leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; Ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's lymphoma; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

In some embodiments, the subject suffers from melanoma. As used herein, "melanoma" refers to a condition characterized by the growth of a tumor arising from the melanocytic system of the skin and other organs. Most melanocytes occur in the skin, but are also found in the meninges, digestive tract, lymph nodes and eyes. When melanoma occurs in the skin, it is referred to as cutaneous melanoma. Melanoma can also occur in the eyes and is called ocular or intraocular melanoma. Melanoma occurs rarely in the meninges, the digestive tract, lymph nodes or other areas where melanocytes are found. 40-60% of melanomas carry an activating mutation in the gene encoding the serine-threonine protein kinase B-RAF (BRAF). Among the BRAF mutations observed in melanoma, over 90% are at codon 600, and among these, over 90% are a single nucleotide mutation resulting in substitution of glutamic acid for valine (BRAFV600E).

In some embodiments, the subject suffers from a melanoma resistant to BRAF inhibitors. As used herein, the term "resistant" refers to the repeated outbreak of melanoma, or a progression of the melanoma independently of whether the disease was cured before said outbreak or progression. As used herein, the term "BRAF inhibitor" refers to an agent that is capable of inhibiting BRAF kinase or mutated BRAF kinase activity (one or more mutated forms of serine-threonine protein kinase B-RAF (BRAF)) (e.g. BRAFV600E). Accordingly, the term "BRAF inhibitors" encompasses within its scope a compound that is capable of inhibiting BRAF or its mutated form; or a compound that is capable of inhibiting V600 mutated form of BRAF. Examples of BRAF inhibitors include but are not limited to BAY43-9006 (sorafenib, Bayer), vemurafenib (PLX4032, Plexxikon; RG7204, RO5185426, Hofmann-LaRoche), GDC-0879 (GlaxoSmithKline), dabrafenib (GSK21 18436, GlaxoSmithKline), PLX4720 (Hofmann-LaRoche), BMS-908662 (XL281, Bristol-Myers Squibb), LGX818 (Novartis), PLX3603 (R05212054, Hofmann-LaRoche), ARQ-736 (ArQule), DP-4978 (Deciphera) or RAF265 (Novartis).

In some embodiments, the subject suffers from a melanoma with elevated plasma lactate dehydrogenase (LDH). Plasma LDH can be considered "elevated" according to the method of the present invention if it exceeds plasma LDH levels typically found in a negative control, i.e., a healthy mammal of the same species. Typically, plasma LDH can be considered "elevated" if it exceeds about 212 IU/mL. Preferably, plasma LDH is considered "elevated" if it exceeds about 250 IU/mL. More preferably, plasma LDH is considered "elevated" if it exceeds about 287 IU/mL.

Accordingly a further object of the present invention relates to a method of treating cancer in a subject in need thereof comprising administering to the subject a therapeutically effective combination of an immune checkpoint inhibitor with a SK1 inhibitor, wherein administration of the combination results in enhanced therapeutic efficacy relative to the administration of the immune checkpoint inhibitor alone.

As used herein, the expression "enhanced therapeutic efficacy," relative to cancer refers to a slowing or diminution of the growth of cancer cells or a solid tumor, or a reduction in the total number of cancer cells or total tumor burden. An "improved therapeutic outcome" or "enhanced therapeutic efficacy" therefore means there is an improvement in the condition of the patient according to any clinically acceptable criteria, including, for example, decreased tumor size, an increase in time to tumor progression, increased progression-free survival, increased overall survival time, an increase in life expectancy, or an improvement in quality of life. In particular, "improved" or "enhanced" refers to an improvement or enhancement of 1%, 5%, 10%, 25% 50%, 75%, 100%, or greater than 100% of any clinically acceptable indicator of therapeutic outcome or efficacy. As used herein, the expression "relative to" when used in the context of comparing the activity and/or efficacy of a combination composition comprising the immune checkpoint inhibitor with the SK1 inhibitor to the activity and/or efficacy of the immune checkpoint alone, refers to a comparison using amounts known to be comparable according to one of skill in the art.

In particular, the method of the present invention is particularly suitable for the treatment of cancer characterized by a low tumor infiltration of CD8+ T cells. Typically said tumor-inflitration of CD8+ T cells is determined by any convention method in the art. For example, said determination comprises quantifying the density of CD8+ T cells in a tumor sample obtained from the subject.

As used herein, the term "tumor tissue sample" means any tissue tumor sample derived from the patient. Said tissue sample is obtained for the purpose of the in vitro evaluation. In some embodiments, the tumor sample may result from the tumor resected from the patient. In some embodiments, the tumor sample may result from a biopsy performed in the primary tumor of the patient or performed in metastatic sample distant from the primary tumor of the patient. For example an endoscopical biopsy performed in the bowel of the patient affected by a colorectal cancer. In some embodiments, the tumor tissue sample encompasses (i) a global primary tumor (as a whole), (ii) a tissue sample from the center of the tumor, (iii) a tissue sample from the tissue directly surrounding the tumor which tissue may be more specifically named the "invasive margin" of the tumor, (iv) lymphoid islets in close proximity with the tumor, (v) the lymph nodes located at the closest proximity of the tumor, (vi) a tumor tissue sample collected prior surgery (for follow-up of patients after treatment for example), and (vii) a distant metastasis. As used herein the "invasive margin" has its general meaning in the art and refers to the cellular environment surrounding the tumor. In some embodiments, the tumor tissue sample, irrespective of whether it is derived from the center of the tumor, from the invasive margin of the tumor, or from the closest lymph nodes, encompasses pieces or slices of tissue that have been removed from the tumor center of from the invasive margin surrounding the tumor, including following a surgical tumor resection or following the collection of a tissue sample for biopsy, for further quantification of one or several biological markers, notably through histology or immunohistochemistry methods, through flow cytometry methods and through methods of gene or protein expression analysis, including genomic and proteomic analysis. The tumor tissue sample can, of course, be subjected to a variety of well-known post-collection preparative and storage techniques (e.g., fixation, storage, freezing, etc.). The sample can be fresh, frozen, fixed (e.g., formalin fixed), or embedded (e.g., paraffin embedded).

In some embodiments, the quantification of density of CD8+ T cells is determined by immunohistochemistry (IHC). For example, the quantification of the density of CD8+ T cells is performed by contacting the tissue tumor tissue sample with a binding partner (e.g. an antibody) specific for a cell surface marker of said cells. Typically, the quantification of density of CD8+ T cells is performed by contacting the tissue tumor tissue sample with a binding partner (e.g. an antibody) specific for CD8. Typically, the density of CD8+ T cells is expressed as the number of these cells that are counted per one unit of surface area of tissue sample, e.g. as the number of cells that are counted per cm' or $mm^2$ of surface area of tumor tissue sample. In some embodiments, the density of cells may also be expressed as the number of cells per one volume unit of sample, e.g. as the number of cells per cm3 of tumor tissue sample. In some embodiments, the density of cells may also consist of the percentage of the specific cells per total cells (set at 100%). Immunohistochemistry typically includes the following steps i) fixing the tumor tissue sample with formalin, ii) embedding said tumor tissue sample in paraffin, iii) cutting said tumor tissue sample into sections for staining, iv) incubating said sections with the binding partner specific for the marker, v) rinsing said sections, vi) incubating said section with a secondary antibody typically biotinylated and vii) revealing the antigen-antibody complex typically with avidin-biotin-peroxidase complex. Accordingly, the tumor tissue sample is firstly incubated the binding partners. After washing, the labeled antibodies that are bound to marker of interest are revealed by the appropriate technique, depending of the kind of label is borne by the labeled antibody, e.g. radioactive, fluorescent or enzyme label. Multiple labelling can be performed simultaneously. Alternatively, the method of the present invention may use a secondary antibody coupled to an amplification system (to intensify staining signal) and enzymatic molecules. Such coupled secondary antibodies are commercially available, e.g. from Dako, EnVision system. Counterstaining may be used, e.g. H&E, DAPI, Hoechst. Other staining methods may be accomplished using any suitable method or system as would be apparent to one of skill in the art, including automated, semi-automated or manual systems. For example, one or more labels can be attached to the antibody, thereby permitting detection of the target protein (i.e the marker). Exemplary labels include radioactive isotopes, fluorophores, ligands, chemiluminescent agents, enzymes, and combinations thereof. In some embmdiments, the label is a quantum dot. Non-limiting examples of labels that can be conjugated to primary and/or secondary affinity ligands include fluorescent dyes or metals (e.g. fluorescein, rhodamine, phycoerythrin, fluorescamine), chromophoric dyes (e.g. rhodopsin), chemiluminescent compounds (e.g. luminal, imidazole) and bioluminescent proteins (e.g. luciferin, luciferase), haptens (e.g. biotin). A variety of other useful fluorescers and chromophores are described in Stryer L (1968) Science 162:526-533 and Brand L and Gohlke J R (1972) Annu. Rev. Biochem. 41:843-868. Affinity ligands can also be labeled with enzymes (e.g. horseradish peroxidase, alkaline phosphatase, beta-lactamase), radioisotopes (e.g. $^3H$, $^{14}C$, $^{32}P$, $^{35}S$ or $^{125}I$) and particles (e.g. gold). The different types of labels can be conjugated to an affinity ligand using various chemistries, e.g. the amine reaction or the thiol reaction. However, other reactive groups than amines and thiols can be used, e.g. aldehydes, carboxylic acids and glutamine. Various enzymatic staining methods are known in the art for detecting a protein of interest. For example, enzymatic interactions can be visualized using different enzymes such as peroxidase, alkaline phosphatase, or different chromogens such as DAB, AEC or Fast Red. In other examples, the antibody can be conjugated to peptides or proteins that can be detected via a labeled binding partner or antibody. In an indirect IHC assay, a secondary antibody or second binding partner is necessary to detect the binding of the first binding partner, as it is not labeled. The resulting stained specimens are each imaged using a system for viewing the detectable signal and acquiring an image, such as a digital image of the staining. Methods for image acquisition are well known to one of skill in the art. For example, once the sample has been stained, any optical or non-optical imaging device can be used to detect the stain or biomarker label, such as, for example, upright or inverted optical microscopes, scanning confocal microscopes, cameras, scanning or tunneling electron microscopes, canning probe microscopes and imaging infrared detectors. In some examples, the image can be captured digitally. The obtained images can then be used for quantitatively or semi-quantitatively determining the amount of the marker in the sample. Various automated sample processing, scanning and analysis systems suitable for use with immunohistochemistry are available in the art. Such systems can include automated staining and microscopic scanning, computerized image analysis, serial section comparison (to control for variation in the orientation and size of a sample), digital report generation, and archiving and tracking of samples (such as slides on which tissue sections are placed). Cellular imaging systems are commercially available that combine conventional light microscopes with digital image processing systems to perform quantitative analysis on cells and tissues, including immunostained samples. See, e.g., the CAS-200 system (Becton, Dickinson & Co.). In particular, detection can be made manually or by image processing techniques involving computer processors and software. Using such software, for example, the images can be configured, calibrated, standardized and/or validated based on factors including, for example, stain quality or stain intensity, using procedures known to one of skill in the art (see e.g., published U.S. Patent Publication No. US20100136549). The image can be quantitatively or semi-quantitatively analyzed and scored based on staining intensity of the sample. Quantitative or semi-quantitative histochemistry refers to method of scanning and scoring samples that have undergone histochemistry, to identify and quantitate the presence of the specified biomarker (i.e. the marker). Quantitative or semi-quantitative methods can employ imaging software to detect staining densities or amount of staining or methods of detecting staining by the human eye, where a trained operator ranks results numerically. For example, images can be quantitatively analyzed using a pixel count algorithms (e.g., Aperio Spectrum Software, Automated QUantitatative Analysis platform (AQUA® platform), and other standard methods that measure or quantitate or semi-quantitate the degree of staining; see e.g., U.S. Pat. Nos. 8,023,714; 7,257,268; 7,219,016; 7,646,905; published U.S. Patent Publication No. US20100136549 and 20110111435; Camp et al. (2002) Nature Medicine, 8:1323-1327; Bacus et al. (1997) Analyt Quant Cytol Histol, 19:316-328). A ratio of strong positive stain (such as brown stain) to the sum of total stained area can be calculated and scored. The amount of the detected biomarker (i.e. the marker) is quantified and given as a percentage of positive pixels and/or a score. For example, the amount can be quantified as a percentage of positive pixels. In some examples, the amount is quantified as the percentage of area stained, e.g., the percentage of positive pixels. For example, a sample can have at least or about at least or about 0, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 40%, 45%, 50%, 55%, 60%, 65%, 70%, 75%, 80%, 85%, 90%, 95% or more positive pixels as compared to the total staining area. In some embodiments, a score is given to the sample that is a numerical representation of the intensity or amount of the histochemical staining of the sample, and represents the amount of target biomarker (e.g., the marker) present in the sample. Optical density or percentage area values can be given a scaled score, for example on an integer scale. Thus, in some embodiments, the method of the present invention comprises the steps consisting in i) providing one or more immunostained slices of tissue section obtained by an automated slide-staining system by using a binding partner capable of selectively interacting with the marker (e.g. an antibody as above described), ii) proceeding to digitalisation of the slides of step a. by high resolution scan capture, iii) detecting the slice of tissue section on the digital picture iv) providing a size reference grid with uniformly distributed units having a same surface, said grid being adapted to the size of the tissue section to be analyzed, and v) detecting, quantifying and measuring intensity of stained cells in each unit whereby the number or the density of cells stained of each unit is assessed.

In some embodiments, the cell density of CD8+ T cells is determined in the whole tumor tissue sample, is determined in the invasive margin or centre of the tumor tissue sample or is determined both in the centre and the invasive margin of the tumor tissue sample.

Accordingly a further object of the present invention relates to a method of treating cancer in a subject in need thereof comprising i) quantifying the density of CD8+ T cells in a tumor tissue sample obtained from the subject ii) comparing the density quantified at step i) with a predetermined reference value and iii) administering to the subject a therapeutically effective combination of an immune checkpoint inhibitor with a SK1 inhibitor when the density quantified at step i) is lower than the predetermined reference value.

Typically, the predetermined reference value correlates with the survival time of the subject. Those of skill in the art will recognize that OS survival time is generally based on and expressed as the percentage of people who survive a certain type of cancer for a specific amount of time. Cancer statistics often use an overall five-year survival rate. In general, OS rates do not specify whether cancer survivors are still undergoing treatment at five years or if they've become cancer-free (achieved remission). DSF gives more specific information and is the number of people with a particular cancer who achieve remission. Also, progression-free survival (PFS) rates (the number of people who still have cancer, but their disease does not progress) includes people who may have had some success with treatment, but the cancer has not disappeared completely. As used herein, the expression "short survival time" indicates that the patient will have a survival time that will be lower than the median (or mean) observed in the general population of patients suffering from said cancer. When the patient will have a short survival time, it is meant that the patient will have a "poor prognosis". Inversely, the expression "long survival time" indicates that the patient will have a survival time that will be higher than the median (or mean) observed in the general population of patients suffering from said cancer. When the patient will have a long survival time, it is meant that the patient will have a "good prognosis".

In some embodiments, the predetermined value is a threshold value or a cut-off value. Typically, a "threshold value" or "cut-off value" can be determined experimentally, empirically, or theoretically. A threshold value can also be arbitrarily selected based upon the existing experimental and/or clinical conditions, as would be recognized by a person of ordinary skilled in the art. For example, retrospective measurement of cell densities in properly banked historical patient samples may be used in establishing the predetermined reference value. The threshold value has to be determined in order to obtain the optimal sensitivity and specificity according to the function of the test and the benefit/risk balance (clinical consequences of false positive and false negative). Typically, the optimal sensitivity and specificity (and so the threshold value) can be determined using a Receiver Operating Characteristic (ROC) curve based on experimental data. For example, after quantifying the density of CD8+ T cells in a group of reference, one can use algorithmic analysis for the statistic treatment of the measured densities in samples to be tested, and thus obtain a classification standard having significance for sample classification. The full name of ROC curve is receiver operator characteristic curve, which is also known as receiver operation characteristic curve. It is mainly used for clinical biochemical diagnostic tests. ROC curve is a comprehensive indicator that reflects the continuous variables of true positive rate (sensitivity) and false positive rate (1-specificity). It reveals the relationship between sensitivity and specificity with the image composition method. A series of different cut-off values (thresholds or critical values, boundary values between normal and abnormal results of diagnostic test) are set as continuous variables to calculate a series of sensitivity and specificity values. Then sensitivity is used as the vertical coordinate and specificity is used as the horizontal coordinate to draw a curve. The higher the area under the curve (AUC), the higher the accuracy of diagnosis. On the ROC curve, the point closest to the far upper left of the coordinate diagram is a critical point having both high sensitivity and high specificity values. The AUC value of the ROC curve is between 1.0 and 0.5. When AUC>0.5, the diagnostic result gets better and better as AUC approaches 1. When AUC is between 0.5 and 0.7, the accuracy is low. When AUC is between 0.7 and 0.9, the accuracy is moderate. When AUC is higher than 0.9, the accuracy is quite high. This algorithmic method is preferably done with a computer. Existing software or systems in the art may be used for the drawing of the ROC curve, such as: MedCalc 9.2.0.1 medical statistical software, SPSS 9.0, ROCPOWER.SAS, DESIGNROC.FOR, MULTIREADER POWER.SAS, CREATE-ROC.SAS, GB STAT VI0.0 (Dynamic Microsystems, Inc. Silver Spring, Md., USA), etc.

In some embodiments, the predetermined reference value is determined by carrying out a method comprising the steps of a) providing a collection of tumor tissue samples from subject suffering from the cancer of interest; b) providing, for each tumor tissue sample provided at step a), information relating to the actual clinical outcome for the corresponding patient (i.e. the duration of the disease-free survival (DFS) and/or the overall survival (OS)); c) providing a serial of arbitrary quantification values; d) quantifying the density of CD8+ T cells for each tumor tissue sample contained in the collection provided at step a); e) classifying said tumor tissue samples in two groups for one specific arbitrary quantification value provided at step c), respectively: (i) a first group comprising tumor tissue samples that exhibit a quantification value for level that is lower than the said arbitrary quantification value contained in the said serial of quantification values; (ii) a second group comprising tumor tissue samples that exhibit a quantification value for said level that is higher than the said arbitrary quantification value contained in the said serial of quantification values; whereby two groups of tumor tissue samples are obtained for the said specific quantification value, wherein the tumor tissue samples of each group are separately enumerated; f) calculating the statistical significance between (i) the quantification value obtained at step e) and (ii) the actual clinical outcome of the patients from which tumor tissue samples contained in the first and second groups defined at step f) derive; g) reiterating steps f) and g) until every arbitrary quantification value provided at step d) is tested; h) setting the said predetermined reference value as consisting of the arbitrary quantification value for which the highest statistical significance (most significant) has been calculated at step g). For example the density of CD8+ T cells has been assessed for 100 tumor tissue samples of 100 patients. The 100 samples are ranked according to the density of CD8+ T cells. Sample 1 has the highest density and sample 100 has the lowest density. A first grouping provides two subsets: on one side sample Nr 1 and on the other side the 99 other samples. The next grouping provides on one side samples 1 and 2 and on the other side the 98 remaining samples etc., until the last grouping: on one side samples 1 to 99 and on the other side sample Nr 100. According to the information relating to the actual clinical outcome for the corresponding cancer patient, Kaplan Meier curves are prepared for each of the 99 groups of two subsets. Also for each of the 99 groups, the p value between both subsets was calculated. The predetermined reference value is then selected such as the discrimination based on the criterion of the minimum p value is the strongest. In other terms, the density of CD8+ T cells corresponding to the boundary between both subsets for which the p value is minimum is considered as the predetermined reference value. It should be noted that the predetermined reference value is not necessarily the median value of cell densities. Thus in some embodiments, the predetermined reference value thus allows discrimination between a poor and a good prognosis with respect to DFS and OS for a patient. Practically, high statistical significance values (e.g. low P values) are generally obtained for a range of successive arbitrary quantification values, and not only for a single arbitrary quantification value. Thus, in one alternative embodiment of the invention, instead of using a definite predetermined reference value, a range of values is provided. Therefore, a minimal statistical significance value (minimal threshold of significance, e.g. maximal threshold P value) is arbitrarily set and a range of a plurality of arbitrary quantification values for which the statistical significance value calculated at step g) is higher (more significant, e.g. lower P value) are retained, so that a range of quantification values is provided. This range of quantification values includes a "cut-off" value as described above. For example, according to this specific embodiment of a "cut-off" value, the outcome can be determined by comparing the density of CD8+ T cells with the range of values which are identified. In some embodiments, a cut-off value thus consists of a range of quantification values, e.g. centered on the quantification value for which the highest statistical significance value is found (e.g. generally the minimum p value which is found).

A further object of the present invention relates to a method of treating cancer in a patient in need thereof comprising administering to the patient a therapeutically effective amount of a SK-1 inhibitor in combination with a cancer vaccine.

As used herein, the term "cancer vaccine" has its general meaning in the art and refers to a composition capable of inducing active immunity against at least one cancer antigen. The cancer vaccine can result in a production of antibodies or simply in the activation of certain cells, in particular antigen-presenting cells, T lymphocytes (in particular T-CD8+ cells) and B lymphocytes. The cancer vaccine can be a composition for prophylactic purposes or for therapeutic purposes or both. As used herein the term "antigen" refers to a molecule capable of being specifically bound by an antibody or by a T cell receptor (TCR) if processed and presented by MHC molecules. The term "antigen", as used herein, also encompasses T-cell epitopes. An antigen is additionally capable of being recognized by the immune system and/or being capable of inducing a humoral immune response and/or cellular immune response leading to the activation of B- and/or T-lymphocytes. An antigen can have one or more epitopes or antigenic sites (B- and T-epitopes). As used herein, the term "cancer antigen" refers to an antigen that is characteristic of a tumor tissue. There are multiple types of cancer vaccines. Non-limiting examples of cancer vaccines include tumor cell vaccines, antigen vaccines, dendritic cell vaccines, DNA vaccines, and vector based vaccines.

Typically, the cancer vaccine of the present invention comprises a tumor-associated antigen ("TAA") or nucleic acid sequence (e.g. DNA) that encodes for a tumor-associated antigen. Numerous tumor-associated antigens are known in the art. Exemplary tumor-associated antigens include, but are not limited to, 5 alpha reductase, alpha-fetoprotein, AM-1, APC, April, BAGE, beta-catenin, Bcll 2, bcr-abl, CA-125, CASP-8/FLICE, Cathepsins, CD19, CD20, CD21, CD23, CD22, CD33 CD35, CD44, CD45, CD46, CD5, CD52, CD55, CD59, CDC27, CDK4, CEA, c-myc, Cox-2, DCC, DcR3, E6/E7, CGFR, EMBP, Dna78, farnesyl transferase, FGF8b, FGF8a, FLK-1/KDR, folic acid receptor, G250, GAGE-family, gastrin 17, gastrin-releasing hormone, GD2/GD3/GM2, GnRH, GnTV, GP1, gp100/Pme117, gp-100-in4, gp15, gp75/TRP-1, hCG, heparanse, Her2/neu, HMTV, Hsp70, hTERT, IGFR1, IL-13R, iNOS, Ki67, KIAA0205, K-ras, H-ras, N-ras, KSA, LKLR-FUT, MAGE-family, mammaglobin, MAP 17, melan-A/MART-1, mesothelin, MIC A B, MT-MMPs, mucin, NY-ESO-1, osteonectin, p15, P170/MDR1, p53, p97/melanotransferrin, PAI-1, PDGF, uPA, PRAME, probasin, progenipoientin, PSA, PSM, RAGE-1, Rb, RCAS1, SART-1, SSX-family, STAT3, STn, TAG-72, TGF-alpha, TGF-beta, Thymosin-beta-15, TNF-alpha, TYRP-, TYRP-2, tyrosinase, VEGF, ZAG, pl6INK4, and glutathione-S-transferase.

In some embodiments, the vaccine is a DNA vaccine. Vectors can be engineered to contain specific DNAs that can be injected into a subject which leads to the DNA being taken up by cells. Once the cells take up the DNA, the DNA will program the cells to make specific antigens, which can then provoke the desired immune response.

In some embodiments, the vaccine consists of a recombinant virus that encodes or express a cancer antigen. In some embodiments, the recombinant virus is a poxvirus expressing a tumor antigen and more particularly an orthopoxvirus such as, but not limited to, a vaccinia virus, a Modified Vaccinia Ankara (MVA) virus, or MVA-BN. Examples of vaccinia virus strains are the strains Temple of Heaven, Copenhagen, Paris, Budapest, Dairen, Gam, MRIVP, Per, Tashkent, TBK, Tom, Bern, Patwadangar, BIEM, B-15, Lister, EM-63, New York City Board of Health, Elstree, Ikeda and WR. A preferred vaccinia virus (W) strain is the Wyeth (DRYVAX) strain (U.S. Pat. No. 7,410,644). Another preferred W strain is a modified vaccinia virus Ankara (MVA) (Sutter, G. et al. [1994], Vaccine 12: 1032-40). Another preferred W strain is MVA-BN. Examples of MVA virus strains that are useful in the practice of the present invention and that have been deposited in compliance with the requirements of the Budapest Treaty are strains MVA 572, deposited at the European Collection of Animal Cell Cultures (ECACC), Vaccine Research and Production Laboratory, Public Health Laboratory Service, Centre for Applied Microbiology and Research, Porton Down, Salisbury, Wiltshire SP4 OJG, United Kingdom, with the deposition number ECACC 94012707 on Jan. 27, 1994, and MVA 575, deposited under ECACC 00120707 on Dec. 7, 2000. MVA-BN, deposited on Aug. 30, 2000 at the European Collection of Cell Cultures (ECACC) under number V00083008, and its derivatives, are additional exemplary strains. In some embodiments, the invention encompasses the use of recombinant orthopoxviruses, preferably a vaccinia virus (W), a Wyeth strain, ACAM 1000, AC AM 2000, MVA, or MVA-BN for cancer therapy. Recombinant orthopoxviruses are generated by insertion of heterologous sequences into an orthopoxvirus. In some embodiments, the recombinant poxvirus expressing a tumor antigen is an avipoxvirus, such as but not limited to a fowlpox virus. The term "avipoxvirus" refers to any avipoxvirus, such as Fowlpoxvirus, Canarypoxvirus, Uncopoxvirus, Mynahpoxvirus, Pigeonpoxvirus, Psittacinepoxvirus, Quailpoxvirus, Peacockpoxvirus, Penguinpoxvirus, Sparrowpoxviras, Starlingpoxviras and Turkeypoxviras. Preferred avipoxviruses are Canarypoxvirus and Fowlpoxvirus.

In some embodiments, the vaccine composition comprises at least one population of antigen presenting cells that present the selected antigen. The antigen-presenting cell (or stimulator cell) typically has an MHC class I or II molecule on its surface, and in one embodiment is substantially incapable of itself loading the MHC class I or II molecule with the selected antigen. Preferably, the antigen presenting cells are dendritic cells. Suitably, the dendritic cells are autologous dendritic cells that are pulsed with the antigen of interest (e.g. a peptide). T-cell therapy using autologous dendritic cells pulsed with peptides from a tumor associated antigen is disclosed in Murphy et al. (1996) The Prostate 29, 371-380 and Tjua et al. (1997) The Prostate 32, 272-278. Thus, in some embodiments, the vaccine composition containing at least one antigen presenting cell is pulsed or loaded with one or more antigenic peptides. As an alternative the antigen presenting cell comprises an expression construct encoding an antigenic peptide. The polynucleotide may be any suitable polynucleotide and it is preferred that it is capable of transducing the dendritic cell, thus resulting in the presentation of a peptide and induction of an immune response.

In some embodiments, the vaccine composition include one or more adjuvants. Adjuvants are substances that non-specifically enhance or potentiate the immune response (e.g., immune responses mediated by CD8-positive T cells and helper-T (TH) cells to an antigen, and would thus be considered useful in the medicament of the present invention. Suitable adjuvants include, but are not limited to, 1018 ISS, aluminum salts, AMPLIVAX®, AS15, BCG, CP-870, 893, CpG7909, CyaA, dSLIM, flagellin or TLRS ligands derived from flagellin, FLT3 ligand, GM-CSF, IC30, IC31, Imiquimod (ALDARA®), resiquimod, ImuFact IMP321, Interleukins as IL-2, IL-13, IL-21, Interferon-alpha or -beta, or pegylated derivatives thereof, IS Patch, ISS, ISCOMATRIX, ISCOMs, Juvlmmune®, LipoVac, MALP2, MF59, monophosphoryl lipid A, Montanide IMS 1312, Montanide ISA 206, Montanide ISA 50V, Montanide ISA-51, water-in-oil and oil-in-water emulsions, OK-432, OM-174, OM-197-MP-EC, ONTAK, OspA, PepTel® vector system, poly(lactid co-glycolid) [PLG]-based and dextran microparticles, talactoferrin SRL172, Virosomes and other Virus-like particles, YF-17D, VEGF trap, R848, beta-glucan, Pam3Cys, Aquila's QS21 stimulon, which is derived from saponin, mycobacterial extracts and synthetic bacterial cell wall mimics, and other proprietary adjuvants such as Ribi's Detox, Quil, or Superfos. Adjuvants such as Freund's or GM-CSF are preferred. Several immunological adjuvants (e.g., MF59) specific for dendritic cells and their preparation have been described previously (Allison and Krummel, 1995). Also cytokines may be used. Several cytokines have been directly linked to influencing dendritic cell migration to lymphoid tissues (e.g., TNF-), accelerating the maturation of dendritic cells into efficient antigen-presenting cells for T-lymphocytes (e.g., GM-CSF, IL-1 and IL-4) (U.S. Pat. No.

5,849,589, specifically incorporated herein by reference in its entirety) and acting as immunoadjuvants (e.g., IL-12, IL-15, IL-23, IL-7, IFN-alpha. IFN-beta) (Gabrilovich et al., 1996).

A further object of the present invention relates to a cancer vaccine comprising an immunoadjuvant together with one or more cancer antigens, for inducing an immune response against said one or more cancer antigens wherein the immunoadjuvant is a SK-1 inhibitor.

The term "sphingosine kinase-1" or "SK1" refers to an enzyme that catalyzes the transformation of sphingosine to sphingosine-1-phosphate (SIP), i.e., phosphorylates sphingosine into S1P. Properties and activities of SK1, e.g., protein sequence of SK1, structural properties of SK1, biochemical properties of SK1, and regulation of SK1, are described in Taha et al. (2006, Journal of Biochemistry and Molecular Biology, 39(2): 113-131). Thus, as used herein the term "SK1 inhibitor" refers to any compound that is capable to inhibit SK1 expression or activity. As used herein the term "SK1 activity" refers to the production, release, expression, function, action, interaction or regulation of SK1, including, e.g., temporal, site or distribution aspects. The activity of SK1 includes modifications, e.g., covalent or non-covalent modifications of SK1 polypeptide, covalent or non-covalent modifications that SK1 induces on other substances, changes in the distribution of SK1 polypeptide, and changes that SK1 induces on the distribution of other substances. Any aspect of SK1 activity can be evaluated. Methods and techniques known to those skilled in the art can be found in various references, e.g., Ausubel et al., ed., Current Protocols in MoI. Biology, New York: John Wiley & Sons, 1990; Sambrook et al., MoI. Cloning, Cold Spring Harbor Laboratory Press, New York, N.Y. (1989). Examples of SK1 activity that can be evaluated include binding activity of SK1 polypeptide to a binding molecule; the effect of SK1 polypeptide on the posttranslational modification or stability of a target gene; the level of SK1 protein; the level of SK1 mRNA; or the level of SK1 modification, e.g., phosphorylation, acetylation, methylation, carboxylation or glycosylation. By binding molecule is meant any molecule to which SK1 can bind, e.g., a nucleic acid, e.g., a DNA regulatory region, a protein, a metabolite, a peptide mimetic, a non-peptide mimetic, an antibody, or any other type of ligand. Binding can be shown, e.g., by electrophoretic mobility shift analysis (EMSA), by the yeast or mammalian two-hybrid or three-hybrid assays, by competition with dimethylspingosine photoaffinity label or biotin-SK1 binding. Transactivation of a target gene by SK1 can be determined, e.g., in a transient transfection assay in which the promoter of the target gene is linked to a reporter gene, e.g., β-galactosidase or luciferase, and co-transfected with a SK1 expression vector. Levels of SK1 protein, mRNA or modification, can, e.g., be measured in a sample, e.g., a tissue sample, e.g., endothelial cells in blood vessels, T and B lymphocytes from blood or lymph organs, heart, muscle or bone joints. In some embodiments, the evaluations are done in vitro; in other embodiments the evaluations are done in vivo.

SK1 inhibitors are well known to the skilled person. For example the skilled person may easily identify such inhibitors from the following patent publications: WO2003105840, WO2006138660, WO2010033701, WO2010078247, WO2010127093, WO2011020116, WO2011072791, WO2012069852, WO2013119946, WO2014118556 and WO2014157382.

In some embodiments, the SK1 inhibitor is selected from the group consisting of 3-(4-Chloro-phenyl)-adamantane-1-carboxylic acid isopropylamide; 3-(4-Chloro-phenyl)-adamantane-1-carboxylic acid cyclopropylamide; 3-(4-Chloro-phenyl)-adamantane-1-carboxylic acid (2-ethylsulfanyl-ethyl)-amide; 3-(4-Chloro-phenyl)-adamantane-1-carboxylic acid phenylamide; Adamantane-1-carboxylic acid (4-hydroxy-phenyl)-amide; 3-(4-Chloro-phenyl)-adamantane-1-carboxylic acid (4-hydroxy-phenyl)-amide; Acetic acid 4-{[3-(4-chloro-phenyl)-adamantane-1-carbonyl]-amino}-phenyl ester; 3-(4-Chloro-phenyl)-adamantane-1-carboxylic acid (2,4-dihydroxy-phenyl)-amide; 3-(4-Chloro-phenyl)-adamantane-1-carboxylic acid (3-hydroxymethyl-phenyl)-amide; Adamantane-1-carboxylic acid (4-cyanomethyl-phenyl)-amide; 3-(4-Chloro-phenyl)-adamantane-1-carboxylic acid (4-cyanomethyl-phenyl)-amide; 3-(4-Chloro-phenyl)-adamantane-1-carboxylic acid benzylamide; 3-(4-Chloro-phenyl)-adamantane-1-carboxylic acid 4-tert-butyl-benzylamide; 3-(4-Chloro-phenyl)-adamantane-1-carboxylic acid 4-methylsulfanyl-benzylamide; 3-(4-Chloro-phenyl)-adamantane-1-carboxylic acid 3-trifluoromethyl-benzylamide; 3-(4-Chloro-phenyl)-adamantane-1-carboxylic acid 4-trifluoromethyl-benzylamide; 3-(4-Chloro-phenyl)-adamantane-1-carboxylic acid 3,5-bis-trifluoromethyl-benzylamide; 3-(4-Chloro-phenyl)-adamantane-1-carboxylic acid 3-fluoro-5-trifluoromethyl-benzylamide; 3-(4-Chloro-phenyl)-adamantane-1-carboxylic acid 2-fluoro-4-trifluoromethyl-benzylamide; 3-(4-Chloro-phenyl)-adamantane-1-carboxylic acid 3,5-difluoro-benzylamide; 3-(4-Chloro-phenyl)-adamantane-1-carboxylic acid 3,4-difluoro-benzylamide; 3-(4-Chloro-phenyl)-adamantane-1-carboxylic acid 3,4,5-trifluoro-benzylamide; 3-(4-Chloro-phenyl)-adamantane-1-carboxylic acid 3-chloro-4-fluoro-benzylamide; 3-(4-Chloro-phenyl)-adamantane-1-carboxylic acid 4-fluoro-3-trifluoromethyl-benzylamide; 3-(4-Chloro-phenyl)-adamantane-1-carboxylic acid 2-chloro-4-fluoro-benzylamide; 3-(4-Chloro-phenyl)-adamantane-1-carboxylic acid 4-chloro-3-trifluoromethyl-benzylamide; 3-(4-Chloro-phenyl)-adamantane-1-carboxylic acid 3-aminomethyl-2,4,5,6-tetrachloro-benzylamide; 3-(4-Chloro-phenyl)-adamantane-1-carboxylic acid [1-(4-chloro-phenyl)-ethyl]-amide; 3-(4-Chloro-phenyl)-adamantane-1-carboxylic acid [1-(4-bromo-phenyl)-ethyl]-amide; 3-(4-Chloro-phenyl)-adamantane-1-carboxylic acid 4-methanesulfonyl-benzylamide; 3-(4-Chloro-phenyl)-adamantane-1-carboxylic acid 4-dimethylamino-benzylamide; 3-(4-Chloro-phenyl)-adamantane-1-carboxylic acid 4-trifluoromethoxy-benzylamide; 3-(4-Chloro-phenyl)-adamantane-1-carboxylic acid 3-trifluoromethoxy-benzylamide; 3-(4-Chloro-phenyl)-adamantane-1-carboxylic acid 4-phenoxy-benzylamide; Adamantane-1-carboxylic acid 3,4-dihydroxy-benzylamide; 3-(4-Chloro-phenyl)-adamantane-1-carboxylic acid 3,4-dihydroxy-benzylamide; 3-(4-Chloro-phenyl)-adamantane-1-carboxylic acid phenethyl-amide; 3-(4-Chloro-phenyl)-adamantane-1-carboxylic acid [2-(4-fluoro-phenyl)-ethyl]-amide; 3-(4-Chloro-phenyl)-adamantane-1-carboxylic acid [2-(4-bromo-phenyl)-ethyl]-amide; 3-(4-Chloro-phenyl)-adamantane-1-carboxylic acid [2-(4-hydroxy-phenyl)-ethyl]-amide; 3-(4-Chloro-phenyl)-adamantane-1-carboxylic acid 4-phenoxy-benzylamide; 3-(4-Chloro-phenyl)-adamantane-1-carboxylic acid [2-(3-bromo-4-methoxy-phenyl)-ethyl]-amide; Adamantane-1-carboxylic acid [2-(3,4-dihydroxy-phenyl)-ethyl]-amide; 3-(4-Chloro-phenyl)-adamantane-1-carboxylic acid [2-(3,4-dihydroxy-phenyl)-ethyl]-amide; 3-(4-Chloro-phenyl)-adamantane-1-carboxylic acid (2-benzo[1,3]dioxol-5-yl-ethyl)-amide; 3-(4-Chloro-phenyl)-adamantane-1-carboxylic acid [2-(3-phenoxy-phenyl)-ethyl]-amide; 3-(4-Chloro-phenyl)- adamantane-1-carboxylic acid [2-(4-phenoxy-phenyl)-ethyl]amide; 3-(4-Chloro-phenyl)-adamantane-1-carboxylic acid (3-phenyl-propyl)-amide; 3-(4-Chloro-phenyl)-adamantane-1-carboxylic acid (biphenyl-4-ylmethyl)-amide; Adamantane-1-carboxylic acid (1-methyl-piperidin-4-yl)-amide; 3-(4-Chloro-phenyl)-adamantane-1-carboxylic acid (1-methyl-piperidin-4-yl)-amide; 3-(4-Chloro-phenyl)-adamantane-1-carboxylic acid (4-methyl-piperazin-1-yl)-amide; 3-(4-Chloro-phenyl)-adamantane-1-carboxylic acid (3-tert-butylamino-propyl)-amide; 3-(4-Chloro-phenyl)-adamantane-1-carboxylic acid (3-pyrrolidin-1-yl-propyl)-amide; 3-(4-Chloro-phenyl)-adamantane-1-carboxylic acid [3-(2-oxo-pyrrolidin-1-yl)-propyl]-amide; Adamantane-1-carboxylic acid [2-(1-methyl-pyrrolidin-2-yl)-ethyl]-amide; 3-(4-Chloro-phenyl)-adamantane-1-carboxylic acid [2-(1-methyl-pyrrolidin-2-yl)-ethyl]-amide; 3-(4-Chloro-phenyl)-adamantane-1-carboxylic acid (2-morpholin-4-yl-ethyl)-amide; 3-(4-Chloro-phenyl)-adamantane-1-carboxylic acid (2-piperazin-1-yl-ethyl)-amide; Adamantane-1-carboxylic acid (pyridin-4-ylmethyl)-amide; 3-(4-Fluoro-phenyl)-adamantane-1-carboxylic acid (pyridin-4-ylmethyl)-amide; 3-(4-Chloro-phenyl)-adamantane-1-carboxylic acid (pyridin-4-ylmethyl)-amide; Adamantane-1-carboxylic acid (pyridin-4-ylmethyl)-amide; 3-(4-Chloro-phenyl)-adamantane-1-carboxylic acid (2-pyridin-4-yl-ethyl)-amide; 3-(4-Chloro-phenyl)-adamantane-1-carboxylic acid (3-imidazol-1-yl-propyl)-amide; 3-(4-Chloro-phenyl)-adamantane-1-carboxylic acid (2-methyl-1H-indol-5-yl)-amide; 3-(4-Chloro-phenyl)-adamantane-1-carboxylic acid (1H-tetrazol-5-yl)-amide; 3-(4-Chloro-phenyl)-adamantane-1-carboxylic acid (9-ethyl-9H-carbazol-3-yl)-amide; Adamantane-1-carboxylic acid [4-(4-chloro-phenyl)-thiazol-2-yl]-amide; 3-(4-Chloro-phenyl)-adamantane-1-carboxylic acid [4-(4-chloro-phenyl)-thiazol-2-yl]-amide; 3-(4-Chloro-phenyl)-adamantane-1-carboxylic acid benzothiazol-2-ylamide; 3-(4-Chloro-phenyl)-adamantane-1-carboxylic acid (5-chloro-benzooxazol-2-yl)-amide; 3-(4-Chloro-phenyl)-adamantane-1-carboxylic acid (9H-purin-6-yl)-amide; [3-(4-Chloro-phenyl)-adamantan-1-ylmethyl]-isopropyl-amine 4-{[3-(4-Chloro-phenyl)-adamantan-1-ylmethyl]-amino}-phenol; [3-(4-Chloro-phenyl)-adamantan-1-ylmethyl]-(4-trifluoromethyl-benzyl)-amine; [3-(4-Chloro-phenyl)-adamantan-1-ylmethyl]-(2-fluoro-4-trifluoromethyl-benzyl)-amine; [3-(4-Chloro-phenyl)-adamantan-1-ylmethyl]-(4-fluoro-3-trifluoromethyl-benzyl)-amine; [3-(4-Chloro-phenyl)-adamantan-1-ylmethyl]-(4-trifluoromethoxy-benzyl)-amine; [3-(4-Chloro-phenyl)-adamantan-1-ylmethyl]-[2-(3-phenoxy-phenyl)-ethyl]-amine; [3-(4-Chloro-phenyl)-adamantan-1-ylmethyl]-(1-methyl-piperidin-4-yl)-amine; [3-(4-Chloro-phenyl)-adamantan-1-ylmethyl]-(4-methyl-piperazin-1-yl)-amine; N-tert-Butyl-N'-[3-(4-chloro-phenyl)-adamantan-1-ylmethyl]-propane-1,3-diamine; [3-(4-Chloro-phenyl)-adamantan-1-ylmethyl]-(3-pyrrolidin-1-yl-propyl)-amine; [3-(4-Chloro-phenyl)-adamantan-1-ylmethyl]-[2-(1-methyl-pyrrolidin-2-yl)-ethyl]-amine; [3-(4-Chloro-phenyl)-adamantan-1-ylmethyl]-(2-morpholin-4-yl-ethyl)-amine; [3-(4-Chloro-phenyl)-adamantan-1-ylmethyl]-pyridin-4-ylmethyl-amine; [3-(4-Chloro-phenyl)-adamantan-1-ylmethyl]-(9-ethyl-9H-carbazol-3-yl)-amine; [3-(4-Chloro-phenyl)-adamantan-1-ylmethyl]-[5-(4-chloro-phenyl)-thiazol-2-yl]-amine; 1-[3-(4-Chloro-phenyl)-adamantan-1-yl]-ethylamine; {1-[3-(4-Chloro-phenyl)-adamantan-1-yl]-ethyl}-isopropyl-amine; Phenyl-[1-(3-phenyl-adamantan-1-yl)-ethyl]-amine; {1-[3-(4-Fluoro-phenyl)-adamantan-1-yl]-ethyl}-phenyl-amine; {1-[3-(4-Chloro-phenyl)-adamantan-1-yl]-ethyl}-phenyl-amine; (1-Adamantan-1-yl-ethyl)-benzyl-amine; Benzyl-[1-(3-phenyl-adamantan-1-yl)-ethyl]-amine; Benzyl-{1-[3-(4-fluoro-phenyl)-adamantan-1-yl]-ethyl}-amine; Benzyl-{1-[3-(4-chloro-phenyl)-adamantan-1-yl]-ethyl}-amine; (4-tert-Butyl-benzyl)-{1-[3-(4-chloro-phenyl)-adamantan-1-yl]-ethyl}-amine; [1-(4-Bromo-phenyl)-ethyl]-{1-[3-(4-chloro-phenyl)-adamantan-1-yl]-ethyl}-amine; (1-Adamantan-1-yl-ethyl)-[2-(4-bromo-phenyl)-ethyl]-amine; [2-(4-Bromo-phenyl)-ethyl]-{1-[3-(4-chloro-phenyl)-adamantan-1-yl]-ethyl}-amine; (1-Adamantan-1-yl-ethyl)-(1-methyl-piperidin-4-yl)-amine; (1-Methyl-piperidin-4-yl)-[1-(3-phenyl-adamantan-1-yl)-ethyl]-amine; {1-[3-(4-Fluoro-phenyl)-adamantan-1-yl]-ethyl}-(1-methyl-piperidin-4-yl)-amine; {1-[3-(4-Chloro-phenyl)-adamantan-1-yl]-ethyl}-(1-methyl-piperidin-4-yl)-amine; {1-[3-(4-Chloro-phenyl)-adamantan-1-yl]-ethyl}-(4-methyl-piperazin-1-yl)-amine; {1-[3-(Phenyl)-adamantan-1-yl]-ethyl}-pyridin-4-ylmethyl-amine; {1-[3-(4-Chloro-phenyl)-adamantan-1-yl]-ethyl}-(6-chloro-pyridin-3-ylmethyl)-amine; {1-[3-(4-Chloro-phenyl)-adamantan-1-yl]-ethyl}-(2-pyridin-4-yl-ethyl)-amine; {1-[3-(4-Chloro-phenyl)-adamantan-1-yl]-ethyl}-(3H-imidazol-4-ylmethyl)-amine; {1-[3-(4-Chloro-phenyl)-adamantan-1-yl]-ethyl}-(2-methyl-1H-indol-5-yl)-amine; {1-[3-(4-Chloro-phenyl)-adamantan-1-yl]-ethyl}-(9-ethyl-9H-carbazol-3-yl)-amine; {1-[3-(4-Chloro-phenyl)-adamantan-1-yl]-ethyl}-(9-ethyl-9H-carbazol-3-ylmethyl)-amine; 9-Ethyl-9H-carbazole-3-carboxylic acid {1-[3-(4-chloro-phenyl)-adamantan-1-yl]-ethyl}-amide; 1-{1-[3-(4-Chloro-phenyl)-adamantan-1-yl]-ethyl}-3-(4-chloro-3-trifluoromethyl-phenyl)-urea; 1-{1-[3-(4-Chloro-phenyl)-adamantan-1-yl]-ethyl}-3-(4-chloro-3-trifluoromethyl-phenyl)-urea; (4-Bromo-thiophen-2-ylmethyl)-{1-[3-(4-chloro-phenyl)-adamantan-1-yl]-ethyl}-amine; and {1-[3-(4-Chloro-phenyl)-adamantan-1-yl]-ethyl}-(4-phenyl-thiophen-2-ylmethyl)-amine.

In some embodiments, the SK1 inhibitor of the present invention is selected from the group consisting of:

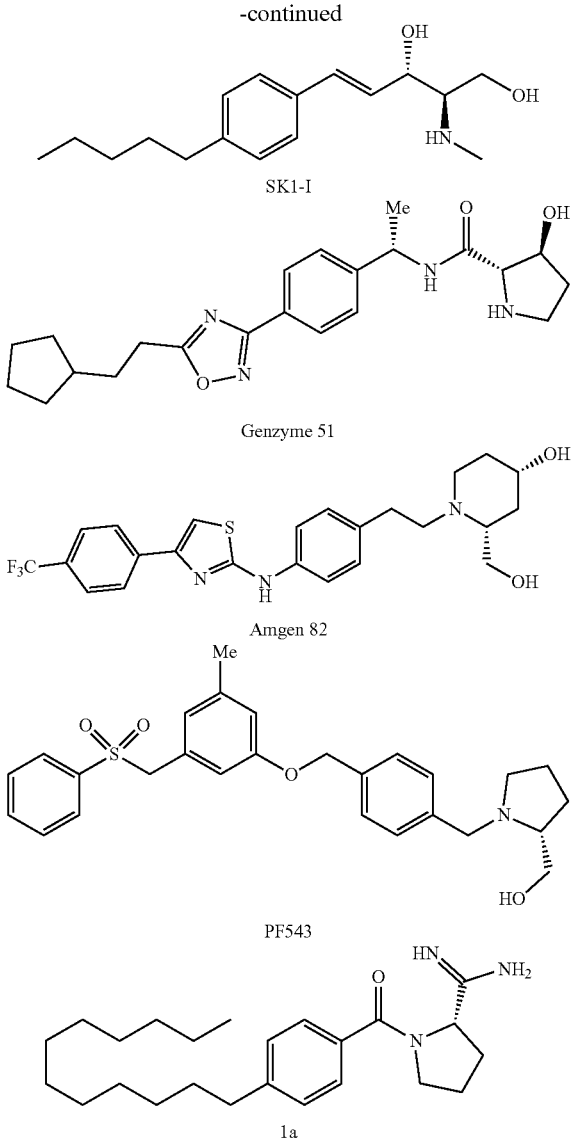

In some embodiments, the SK1 inhibitor is N'-[(2-hydroxynaphthalen-1-yl)methylidene]-3-(naphthalen-2-yl)-1H-pyrazole-5-carbohydrazide having the formula of:

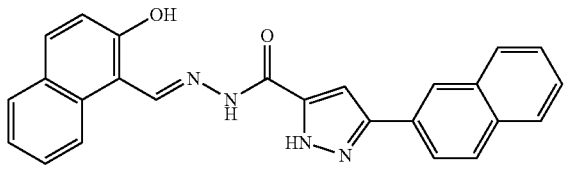 [SMILES: O=C(N/N=C/c1c(O)ccc2ccccc12)c1cc(-c2ccc3ccccc3c2)n[nH]1]

In some embodiments, the SK1 inhibitor is an inhibitor of SK1 expression. An "inhibitor of expression" refers to a natural or synthetic compound that has a biological effect to inhibit the expression of a gene. In a preferred embodiment of the invention, said inhibitor of gene expression is a siRNA, an antisense oligonucleotide or a ribozyme. For example, anti-sense oligonucleotides, including anti-sense RNA molecules and anti-sense DNA molecules, would act to directly block the translation of SK1 mRNA by binding thereto and thus preventing protein translation or increasing mRNA degradation, thus decreasing the level of SK1, and thus activity, in a cell. For example, antisense oligonucleotides of at least about 15 bases and complementary to unique regions of the mRNA transcript sequence encoding SK1 can be synthesized, e.g., by conventional phosphodiester techniques. Methods for using antisense techniques for specifically inhibiting gene expression of genes whose sequence is known are well known in the art (e.g. see U.S. Pat. Nos. 6,566,135; 6,566,131; 6,365,354; 6,410,323; 6,107,091; 6,046,321; and 5,981,732). Small inhibitory RNAs (siRNAs) can also function as inhibitors of expression for use in the present invention. SK1 gene expression can be reduced by contacting a subject or cell with a small double stranded RNA (dsRNA), or a vector or construct causing the production of a small double stranded RNA, such that SK1 gene expression is specifically inhibited (i.e. RNA interference or RNAi). Antisense oligonucleotides, siRNAs, shRNAs and ribozymes of the invention may be delivered in vivo alone or in association with a vector. In its broadest sense, a "vector" is any vehicle capable of facilitating the transfer of the antisense oligonucleotide, siRNA, shRNA or ribozyme nucleic acid to the cells and typically cells expressing SK1. Typically, the vector transports the nucleic acid to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the antisense oligonucleotide, siRNA, shRNA or ribozyme nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rous sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art.

In some embodiments, the immune checkpoint inhibitor is an antibody selected from the group consisting of anti-CTLA4 antibodies, anti-PD-1 antibodies, anti-PD-L1 antibodies, anti-PD-L2 antibodies anti-TIM-3 antibodies, anti-LAG3 antibodies, anti-B7H3 antibodies, anti-B7H4 antibodies, anti-BTLA antibodies, and anti-B7H6 antibodies.

As used herein, the term "antibody" is thus used to refer to any antibody-like molecule that has an antigen binding region, and this term includes antibody fragments that comprise an antigen binding domain such as Fab', Fab, F(ab')2, single domain antibodies (DABs), TandAbs dimer, Fv, scFv (single chain Fv), dsFv, ds-scFv, Fd, linear antibodies, minibodies, diabodies, bispecific antibody fragments, bibody, tribody (scFv-Fab fusions, bispecific or trispecific, respectively); sc-diabody; kappa(lamda) bodies (scFv-CL fusions); BiTE (Bispecific T-cell Engager, scFv-scFv tandems to attract T cells); DVD-Ig (dual variable domain antibody, bispecific format); SIP (small immunoprotein, a kind of minibody); SMIP ("small modular immunopharmaceutical" scFv-Fc dimer; DART (ds-stabilized diabody "Dual Affinity ReTargeting"); small antibody mimetics comprising one or more CDRs and the like. The techniques for preparing and using various antibody-based constructs and fragments are well known in the art (see Kabat et al., 1991, specifically incorporated herein by reference). Diabodies, in particular, are further described in EP 404, 097 and WO 93/11161; whereas linear antibodies are further described in Zapata et al. (1995). Antibodies can be fragmented using conventional techniques. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments. Fab, Fab' and F(ab')2, scFv, Fv, dsFv, Fd, dAbs, TandAbs, ds-scFv, dimers, minibodies, diabodies, bispecific antibody fragments and other fragments can also be synthesized by recombinant techniques or can be chemically synthesized. Techniques for producing antibody fragments are well known and described in the art. For example, each of Beckman et al., 2006; Holliger & Hudson, 2005; Le Gall et al., 2004; Reff & Heard, 2001; Reiter et al., 1996; and Young et al., 1995 further describe and enable the production of effective antibody fragments. In some embodiments, the antibody of the present invention is a single chain antibody. As used herein the term "single domain antibody" has its general meaning in the art and refers to the single heavy chain variable domain of antibodies of the type that can be found in Camelid mammals which are naturally devoid of light chains. Such single domain antibody are also "Nanobody®". For a general description of (single) domain antibodies, reference is also made to the prior art cited above, as well as to EP 0 368 684, Ward et al. (Nature 1989 Oct. 12; 341 (6242): 544-6), Holt et al., Trends Biotechnol., 2003, 21(11):484-490; and WO 06/030220, WO 06/003388.

In some embodiments, the antibody is a humanized antibody. As used herein, "humanized" describes antibodies wherein some, most or all of the amino acids outside the CDR regions are replaced with corresponding amino acids derived from human immunoglobulin molecules. Methods of humanization include, but are not limited to, those described in U.S. Pat. Nos. 4,816,567, 5,225,539, 5,585,089, 5,693,761, 5,693,762 and 5,859,205, which are hereby incorporated by reference.

In some embodiments, the antibody is a fully human antibody. Fully human monoclonal antibodies also can be prepared by immunizing mice transgenic for large portions of human immunoglobulin heavy and light chain loci. See, e.g., U.S. Pat. Nos. 5,591,669, 5,598,369, 5,545,806, 5,545,807, 6,150,584, and references cited therein, the contents of which are incorporated herein by reference. These animals have been genetically modified such that there is a functional deletion in the production of endogenous (e.g., murine) antibodies. The animals are further modified to contain all or a portion of the human germ-line immunoglobulin gene locus such that immunization of these animals will result in the production of fully human antibodies to the antigen of interest. Following immunization of these mice (e.g., XenoMouse (Abgenix), HuMAb mice (Medarex/GenPharm)), monoclonal antibodies can be prepared according to standard hybridoma technology. These monoclonal antibodies will have human immunoglobulin amino acid sequences and therefore will not provoke human anti-mouse antibody (KAMA) responses when administered to humans. In vitro methods also exist for producing human antibodies. These include phage display technology (U.S. Pat. Nos. 5,565,332 and 5,573,905) and in vitro stimulation of human B cells (U.S. Pat. Nos. 5,229,275 and 5,567,610). The contents of these patents are incorporated herein by reference.

In some embodiments, the antibody comprises human heavy chain constant regions sequences but will not deplete CD8+ T cells to which they are bound and preferably do not comprise an Fc portion that induces antibody dependent cellular cytotoxicity (ADCC). As used herein, the term "depleting", with respect to CD8+ T cells means a process, method, or compound that can kill, eliminate, lyse or induce such killing, elimination or lysis, so as to negatively affect the number of CD8+ T cells present in a sample or in a subject. The terms "Fc domain," "Fc portion," and "Fc region" refer to a C-terminal fragment of an antibody heavy chain, e.g., from about amino acid (aa) 230 to about aa 450 of human gamma heavy chain or its counterpart sequence in other types of antibody heavy chains (e.g., α, δ, ε and µ for human antibodies), or a naturally occurring allotype thereof. Unless otherwise specified, the commonly accepted Kabat amino acid numbering for immunoglobulins is used throughout this disclosure (see Kabat et al. (1991) Sequences of Protein of Immunological Interest, 5th ed., United States Public Health Service, National Institute of Health, Bethesda, Md.). In some embodiments the antibody of the present invention does not lead, directly or indirectly, to the depletion of CD8+ T cells (e.g. do not lead to a 10%, 20%, 50%, 60% or greater elimination or decrease in number CD8+ T cells). In some embodiments, the antibody of the present invention does not comprise an Fc domain capable of substantially binding to a FcgRIIIA (CD16) polypeptide. In some embodiments, the antibody of the present invention lacks an Fc domain (e.g. lacks a CH2 and/or CH3 domain) or comprises an Fc domain of IgG2 or IgG4 isotype. In some embodiments, the antibody of the present invention consists of or comprises a Fab, Fab', Fab'-SH, F (ab') 2, Fv, a diabody, single-chain antibody fragment, or a multispecific antibody comprising multiple different antibody fragments. In some embodiments, the antibody of the present invention is not linked to a toxic moiety. In some embodiments, one or more amino acids selected from amino acid residues can be replaced with a different amino acid residue such that the antibody has altered C2q binding and/or reduced or abolished complement dependent cytotoxicity (CDC). This approach is described in further detail in U.S. Pat. No. 6,194,551 by Idusogie et al.

Examples of anti-CTLA-4 antibodies are described in U.S. Pat. Nos. 5,811,097; 5,811,097; 5,855,887; 6,051,227; 6,207,157; 6,682,736; 6,984,720; and 7,605,238. One anti-CTLA-4 antibody is tremelimumab, (ticilimumab, CP-675, 206). In some embodiments, the anti-CTLA-4 antibody is ipilimumab (also known as 10D1, MDX-D010) a fully human monoclonal IgG antibody that binds to CTLA-4.

Examples of PD-1 and PD-L1 antibodies are described in U.S. Pat. Nos. 7,488,802; 7,943,743; 8,008,449; 8,168,757; 8,217,149, and PCT Published Patent Application Nos: WO03042402, WO2008156712, WO2010089411, WO2010036959, WO2011066342, WO2011159877, WO2011082400, and WO2011161699. In some embodiments, the PD-1 blockers include anti-PD-L1 antibodies. In certain other embodiments the PD-1 blockers include anti-PD-1 antibodies and similar binding proteins such as nivolumab (MDX 1106, BMS 936558, ONO 4538), a fully human IgG4 antibody that binds to and blocks the activation of PD-1 by its ligands PD-L1 and PD-L2; lambrolizumab (MK-3475 or SCH 900475), a humanized monoclonal IgG4 antibody against PD-1; CT-011 a humanized antibody that binds PD-1; AMP-224 is a fusion protein of B7-DC; an antibody Fc portion; BMS-936559 (MDX-1105-01) for PD-L1 (B7-H1) blockade.

Other immune-checkpoint inhibitors include lymphocyte activation gene-3 (LAG-3) inhibitors, such as IMP321, a soluble Ig fusion protein (Brignone et al., 2007, J. Immunol. 179:4202-4211). Other immune-checkpoint inhibitors include B7 inhibitors, such as B7-H3 and B7-H4 inhibitors. In particular, the anti-B7-H3 antibody MGA271 (Loo et al., 2012, Clin. Cancer Res. July 15 (18) 3834). Also included are TIM3 (T-cell immunoglobulin domain and mucin domain 3) inhibitors (Fourcade et al., 2010, J. Exp. Med. 207:2175-86 and Sakuishi et al., 2010, J. Exp. Med. 207: 2187-94). As used herein, the term "TIM-3" has its general meaning in the art and refers to T cell immunoglobulin and mucin domain-containing molecule 3. The natural ligand of TIM-3 is galectin 9 (Gal9). Accordingly, the term "TIM-3 inhibitor" as used herein refers to a compound, substance or composition that can inhibit the function of TIM-3. For example, the inhibitor can inhibit the expression or activity of TIM-3, modulate or block the TIM-3 signaling pathway and/or block the binding of TIM-3 to galectin-9. Antibodies having specificity for TIM-3 are well known in the art and typically those described in WO2011155607, WO2013006490 and WO2010117057.

In some embodiments, the immune checkpoint inhibitor is an IDO inhibitor. Examples of IDO inhibitors are described in WO 2014150677. Examples of IDO inhibitors include without limitation 1-methyl-tryptophan (IMT), β-(3-benzofuranyl)-alanine, β-(3-benzo(b)thienyl)-alanine), 6-nitro-tryptophan, 6-fluoro-tryptophan, 4-methyl-tryptophan, 5-methyl tryptophan, 6-methyl-tryptophan, 5-methoxy-tryptophan, 5-hydroxy-tryptophan, indole 3-carbinol, 3,3'-diindolylmethane, epigallocatechin gallate, 5-Br-4-Cl-indoxyl 1,3-diacetate, 9-vinylcarbazole, acemetacin, 5-bromo-tryptophan, 5-bromoindoxyl diacetate, 3-Amino-naphtoic acid, pyrrolidine dithiocarbamate, 4-phenylimidazole a brassinin derivative, a thiohydantoin derivative, a β-carboline derivative or a brassilexin derivative. Preferably the IDO inhibitor is selected from 1-methyl-tryptophan, β-(3-benzofuranyl)-alanine, 6-nitro-L-tryptophan, 3-Amino-naphtoic acid and β-[3-benzo(b)thienyl]-alanine or a derivative or prodrug thereof.

As used herein the term "co-administering" as used herein means a process whereby the combination of the SK1 inhibitor and the immune checkpoint inhibitor, is administered to the same patient. The SK1 inhibitor and the immune checkpoint inhibitor may be administered simultaneously, at essentially the same time, or sequentially. If administration takes place sequentially, the SK1 inhibitor is administered before the immune checkpoint inhibitor. The SK1 inhibitor and the immune checkpoint inhibitor need not be administered by means of the same vehicle. The SK1 inhibitor and the immune checkpoint inhibitor may be administered one or more times and the number of administrations of each component of the combination may be the same or different. In addition, the SK1 inhibitor and the immune checkpoint inhibitor need not be administered at the same site.

As used herein, the term "therapeutically effective combination" as used herein refers to an amount or dose of a SK1 inhibitor together with the amount or dose of the immune checkpoint inhibitor that is sufficient to treat the disease (e.g. cancer). The amount of the SK1 inhibitor in a given therapeutically effective combination may be different for different individuals and different tumor types, and will be dependent upon the one or more additional agents or treatments included in the combination. The "therapeutically effective amount" is determined using procedures routinely employed by those of skill in the art such that an "improved therapeutic outcome" results. It will be understood, however, that the total daily usage of the compounds and compositions of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidential with the specific polypeptide employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Typically, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

According to the invention, the SK1 inhibitor and the immune checkpoint inhibitor are administered to the subject in the form of a pharmaceutical composition. Typically, the SK1 inhibitor and the immune checkpoint inhibitor may be combined with pharmaceutically acceptable excipients, and optionally sustained-release matrices, such as biodegradable polymers, to form therapeutic compositions. "Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type. In the pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms. Typically, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions. The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms. The SK1 inhibitor and the immune checkpoint inhibitor can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin. Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the typical methods of preparation are vacuum-drying and freeze-drying techniques which yield a powder of the active ingredient plus any additional desired ingredient from a previously sterile-filtered solution thereof. The preparation of more, or highly concentrated solutions for direct injection is also contemplated, where the use of DMSO as solvent is envisioned to result in extremely rapid penetration, delivering high concentrations of the active agents to a small tumor area. Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. Some variation in dosage will necessarily occur depending on the condition of the subject being treated. The person responsible for administration will, in any event, determine the appropriate dose for the individual subject.

The invention will be further illustrated by the following figures and examples. However, these examples and figures should not be interpreted in any way as limiting the scope of the present invention.

FIGURES

FIG. 1. Downregulation of SK1 reduces melanoma tumor development in mice. (A), SK1 enzymatic activity was measured in Yumm cells stably transfected with a control (shCtrl) or two SK1-targeted shRNA: shSK1 and shSK1(2). Enzyme activity (calculated as pmol/min/mg of proteins) in cells transfected with shSK1 is compared to that of shCtrl cells. Data are means±sem of 3 independent experiments. (B-D), shCtrl or shSK1 Yumm cells (3.105) were injected in the dermis of wild-type (WT) C57BL/6 mice (B and C) or CD8-deficient mice (D). Tumor volume was determined at the indicated days (B and D) or at the end of the experiment (C, day 26). Growth profiles are presented as mean of tumor volume±SEM and are representative of at least two independent experiments. (B and C n=12 per group, D n=8 per group). Samples were compared using Mann-Whitney test. $*p<0.05$, $p<0.01$, $*p<0.001$.

FIG. 2. Downregulation of SK1 increases CD8+ T cell proliferation and activation and inversely, reduces Treg. shCtrl or shSK1 Yumm murine melanoma cells were injected in C57BL/6 mice and TILs were analyzed on day 11 by using flow cytometry. (A) CD8+, Foxp3+CD4+(Treg) and Foxp3-CD4+ T cells percentages and CD8+/Treg ratio in tumors at day 11. (B and C) The proportion of CD8+(B) and Treg cells (C) expressing Ki67, PD-1 and CTLA-4 was evaluated. Each symbol represents an independent tumor (n=9 mice per group). Results are representative of at least 2 independent experiments. Samples were compared using Mann-Whitney test. $*p<0.05$, $p<0.01$, $*p<0.001$.

FIG. 3. Downregulation of SK1 in tumor cells enhances the efficacy of anti-CTLA-4 or anti-PD-1 therapy. Mice were challenged with 3.105 shCtrl or shSK1 Yumm cells on day 0, and then treated with control antibody (upper panels), α-CTLA-4 (days 7, 10 and 13) or/and α-PD-1 (days 5, 7 and 10). (A and B) Individual curves are depicted for each tumor (n=6-11 mice per group). Inserts: numbers indicate percentage of tumor-free mice at day 25. (C) Cumulative survival curves (Logrank test: $*p<0.05$; $p<0.01$; $*p<0.001$). (D) CD8/Treg ratio in tumors at day 11 are represented as Tukey box (n=10 per group). Results are representative of at least 2 independent experiments. Samples were compared using Mann-Whitney test. $*p<0.05$, $p<0.01$, $*p<0.001$.

Figure 4:
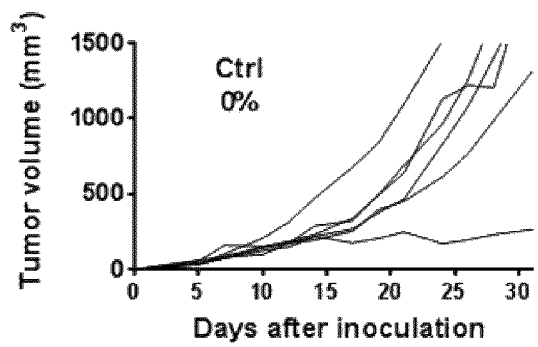
Figure 4:
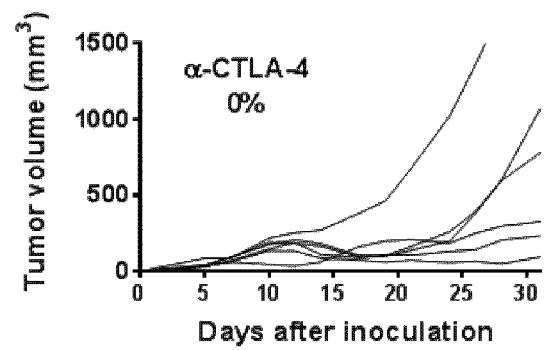
Figure 4:
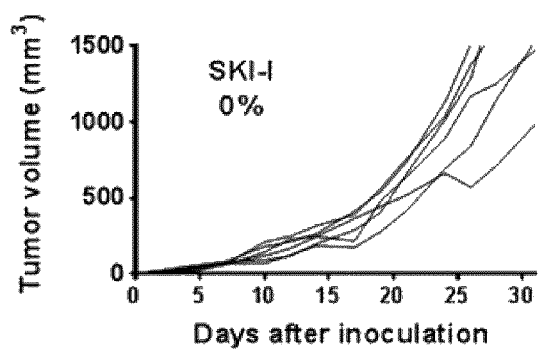
Figure 4:
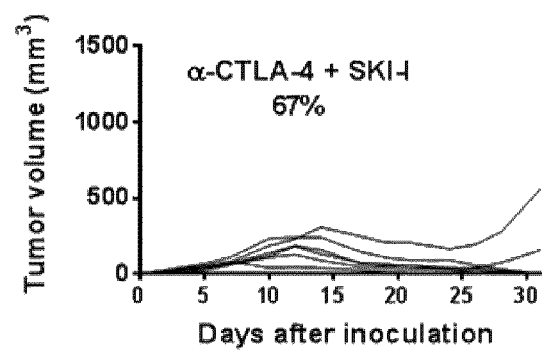
Figure 4:
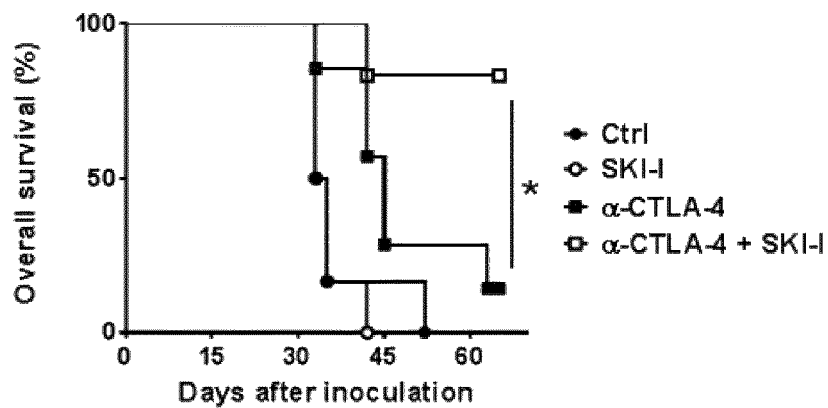

FIG. 4. Pharmacological inhibition of SK1 synergizes with CTLA-4 blockade to eradicate melanoma tumors. Mice were challenged with 3.105 untransfected Yumm cells on day 0, and then treated or not with SKI-I on days 5, 7, 10, 13 and 15. Control antibody or α-CTLA-4 was injected on days 7, 10 and 13. (A) Tumor volumes determined at the indicated days for individual tumors are depicted (n=6 mice per group). Inserts: numbers indicate percentage of tumor-free mice at day 30. (B) Cumulative survival curves (Logrank test: $*p<0.05$).

Figure 5:
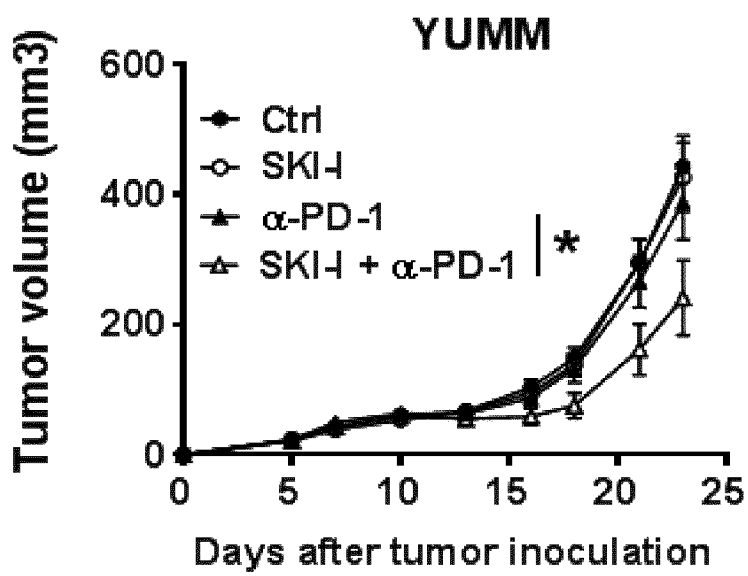
Figure 5:
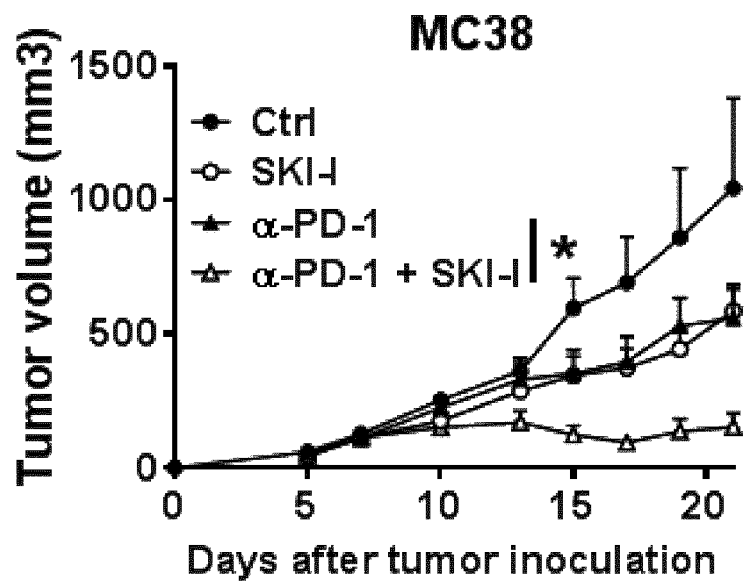

FIG. 5. Pharmacological inhibition of SK1 synergizes with anti-PD-1 blockade to reduce tumor growth in melanoma and colon carcinoma. (A) Mice were challenged with 3.105 untransfected Yumm cells on day 0, and then treated or not with SKI-I on days 5, 7, 10, 13 and 15. Control antibody or α-PD-1 was injected on days 5, 7 and 10 (n=11-12 mice per group). (B) Mice were inoculated with 3.105 MC38 cells on day 0, and then treated or not with SKI-I on days 5, 7, 10, 13 and 15. Control antibody or α-PD-1 was injected on days 7 and 10 (n=4-6 mice per group). Tumor volume (means±sem for each group) was determined at the indicated days. Samples were compared using Mann-Whitney test. *p<0.05.

EXAMPLE

Material & Methods

Cell Culture

Yumm murine melanoma cells, which harbor BRAFV600E mutation, Pten and Cdkn2a deletion [1] were kindly provided by Dr. S. Tartare-Deckert (INSERM U1065 Nice, France). Yumm cells were grown as monolayers in OptiMEM media supplemented with 3% heat-inactivated fetal calf serum (FCS) in the presence of 5% $CO_2$ in a humidified atmosphere at 37° C. To guarantee cell line authenticity, Yumm cell lines were used for a limited number of passages and routinely tested for the expression of melanocyte-lineage proteins such as MelanA/MART1. MC38 cells were kindly provided by Drs T. Chardes et A. Pélegrin (INSERM U1194, Montpellier, France) and were cultured in DMEM containing 10% FCS, 2 mM glutamine, 0.1 mM non essential amino acids, 1 mM sodium pyruvate and 10 mM Hepes.

Cell Transfection

Yumm cells were co-transfected, in a 1:10 ratio, with the pEGFP-N empty vector and a SK1 shRNA (shSK1 or shSK1(2)) plasmid (shRNA from Thermoscientific) or a control non-targeting shRNA (shCtrl) plasmid (pLK01, Addgene). In brief, 500,000 cells were seeded in T25 cell culture flasks. Plasmids were diluted in OptiMEM (Thermofisher) medium without serum. Cells were transfected with 10 μg shRNA oligomer using Lipofectamine 2000 reagent (Invitrogen) according to the manufacturer's instructions. Transfected cells were selected with 0.4 mg/ml G418 and 1.5 μg/ml puromycin and GFP-expressing cells were sorted by FACS. Stable transfectants were maintained in media containing 1 μg/ml puromycin; for the experiments, cells were cultured in medium without puromycin.

SK1 Enzymatic Assay

SK1 activity was determined as described (Lavieu, Scarlatti et al. 2008) with minor modifications.

Tumor Cell Injections and Treatments in Mice

Animal experiments were conducted in accordance with national and international policies, and our protocol was approved by the Regional Ethics Committee of Midi-Pyrenees. 3.105 of Yumm cell lines (Untransfected, shCtrl, shSK1 or shSK1(2)) were intradermally injected into the flank of 7-week-old C57BL/6 mice (Charles River, L'Arbresle, France). CD8-deficient C57BL/6 mice were a gift from Prof. J. van Meerwijk (INSERM U1043, Toulouse, France). Tumor volume was calculated using a caliper at the indicated days as described (Albinet, Bats et al. 2014). For combination experiments involving shCtrl or shSK1 Yumm cells, mice were challenged intradermally (i.d.) with 3.105 cells on day 0 on their right flank. Mice were then injected i.p. three times with anti-CTLA-4 (200 μg per mouse on D7 and 100 μg per mouse on D10 and D13), and/or with anti-PD-1 or isotype control antibody (200 μg per mouse on D5, D7 and D10). Tumor volumes were measured every 2-3 days. Anti-CTLA-4 (9H10), anti-PD-1 (RMP1-14) and isotype control (2A3) were purchased from BioXcell.

For SKI-I treatment, 5 days after Yumm or MC38 cell implantation, mice were treated or not with 50 mg/kg SKI-I (N'-[(2-hydroxynaphthalen-1-yl)methylidene]-3-(naphthalen-2-yl)-1H-pyrazole-5-carbohydrazide, Enamine) in 50 μl of a mixture of DMSO (10%), Cremophor (5%), Tween-80 (5%) and glucose (80%) (i.p.). Mice received additional treatments of SKI-I on days 7, 10, 13 and 15. Mice with Yumm tumors were injected i.p. with anti-CTLA-4 or anti-PD-1 or control antibody as described above. For MC38 tumors, mice were injected i.p. two times with anti-PD-1 (100 μg per mouse on D7 and D10).

Analysis of Leukocyte Content in Tumors

Yumm cells (3.105) were intradermally injected into C57BL/6 mice. At day 11, mice were sacrificed and tumors were collected and digested with Mouse Tumor Dissociation kit and GentleMacs (Miltenyi). Cells were counted and stained with the indicated antibodies and LIVE/DEAD reactive dyes (Invitrogen) prior to flow cytometry analysis (BD LSRFortessa X-20). Analyses were restricted to viable cells and performed using anti-mouse CD45 (BD Biosciences), anti-mouse Thy1 (Biolegend), anti-mouse CD8 (Biolegend), anti-mouse CD4 (BD Biosciences), anti-mouse Foxp3 (eBioscience), anti-mouse Ki-67 (BD Bioscience), anti-mouse PD-1 (eBioscience) or anti-mouse CTLA-4 (eBioscience). Isotype controls were from BD Biosciences, Biolegend or eBioscience.

Statistical Analyses

Data were analysed using GraphPad Prism (GraphPad Software, San Diego, Calif.). Results are expressed as means±sem. Student's t test was used for statistical comparisons among groups and differences were considered statistically significant when $p<0.05$ (*, $p<0.05$; , $p<0.01$; *, $p<0.001$). Tumor survival data were analyzed with the Kaplan-Meier method. The log-rank test was used to compare survival curves for different subgroups on univariate analyses.

Results

SK1 Downregulation Reduces Tumor Growth and Enhances Antitumor Responses to Melanoma In order to evaluate the effect of SK1 in a syngeneic C57BL/6 mouse model of melanoma, we used a transplantable tumor cell line (Yumm cells) established from a BrafV600E/+; Pten–/–; CDKN2A–/– mouse (Pencheva, Buss et al. 2014). We generated stable SK1 knockdown Yumm cells, by using a shRNA-mediated silencing technology. We obtained two puromycin-resistant cell lines; shSK1 and shSK1(2), exhibiting a markedly reduced enzymatic activity of SK1 (around 60% inhibition) (FIG. 1A). Then, Yumm cells, SK1 knockdown or not (shCtrl) for SK1, were intradermally injected in C57BL/6 mice, and tumor growth was monitored. The tumor growth of shSK1 and shSK1(2) Yumm cells was significantly lower than that of shCtrl Yumm cells (FIGS. 1B and C). Interestingly, a tumor regression after day 11 was observed in WT mice injected with ShSK1 cells that could reflect an increased anti-melanoma immune response. However, this effect was unlikely sufficient to obtain a long-lasting immune response, presumably due to immune escape mechanisms. Importantly, SK1 knockdown failed to impair Yumm melanoma growth in CD8-deficient mice (FIG. 1D).

Figure 2A:
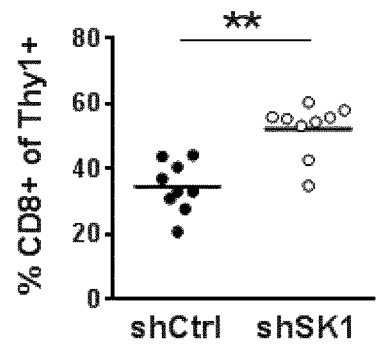
Figure 2A:
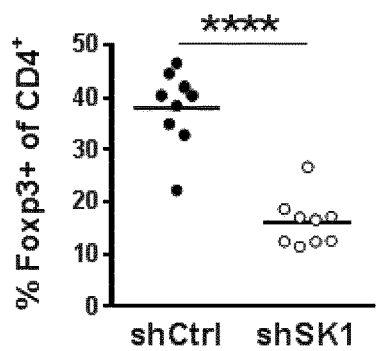
Figure 2A:
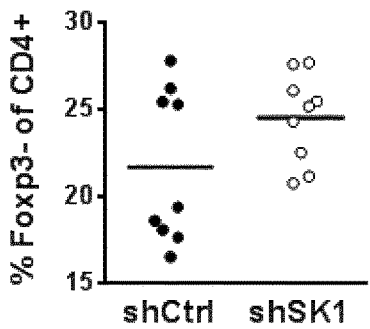
Figure 2A:
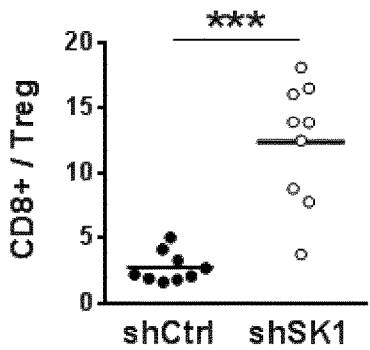
Figure 2B:
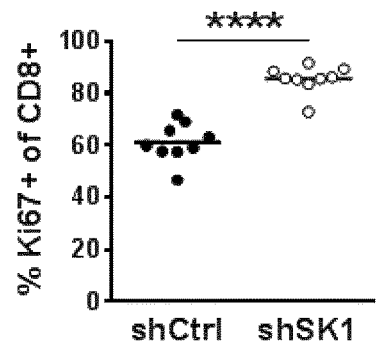
Figure 2B:
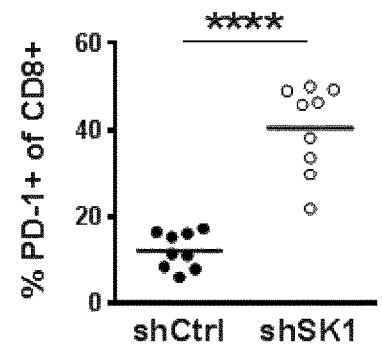
Figure 2B:
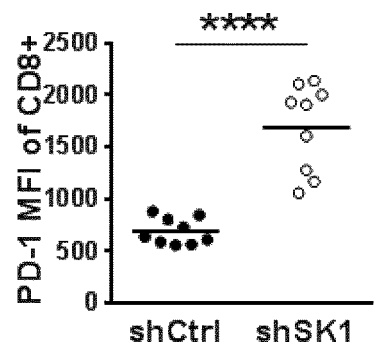
Figure 2B:
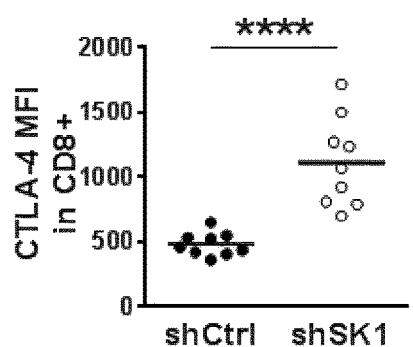
Figure 2C:
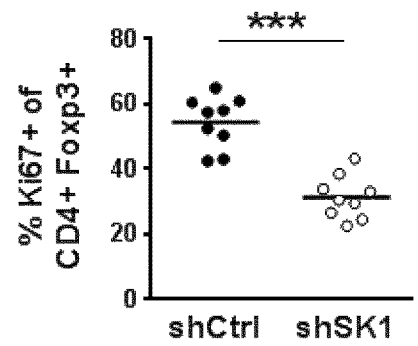
Figure 2C:
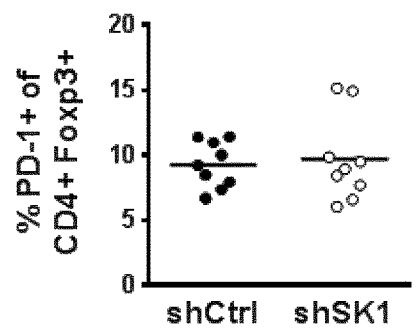
Figure 2C:
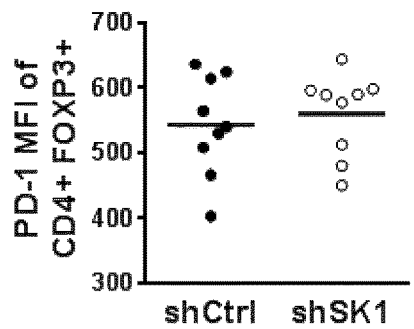
Figure 2C:
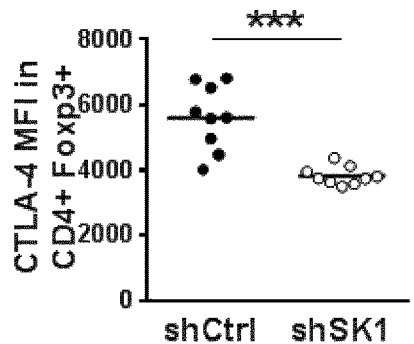

To evaluate the impact of SK1 downregulation on the composition of intratumoral lymphocyte infiltrate, we analyzed Tumor Infiltrating Lymphocytes (TIL) on day 11. Of interest was the finding that SK1 downregulation increased the proportion of CD8+ T cells and decreased the proportion of Foxp3+CD4+ T cells (Treg) leading to a 4-fold increase in CD8/Treg ratio (FIG. 2A). Moreover, the analysis of TIL proliferation (as evaluated by monitoring Ki67 expression) and activation (as evaluated by PD-1 and CTLA-4 expression) showed that SK1 knockdown significantly increased CD8+ T cell proliferation and activation (FIG. 2B) and inversely, decreased Treg proliferation as well as CTLA-4 expression (FIG. 2C).

SK1 Downregulation Improves the Response to Immunotherapy

Figure 3A:
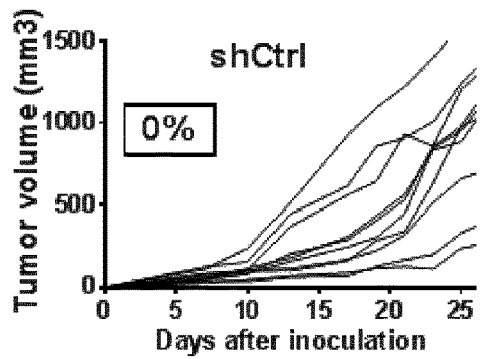
Figure 3A:
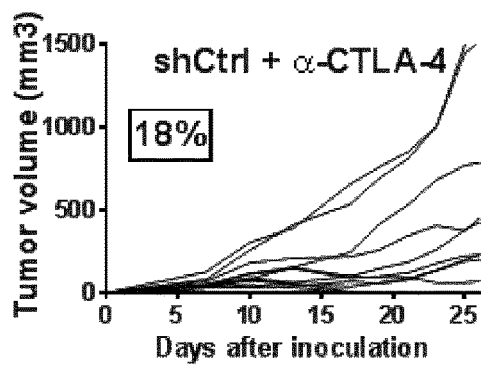
Figure 3A:
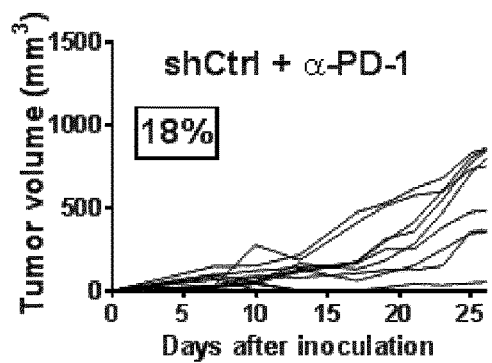
Figure 3A:
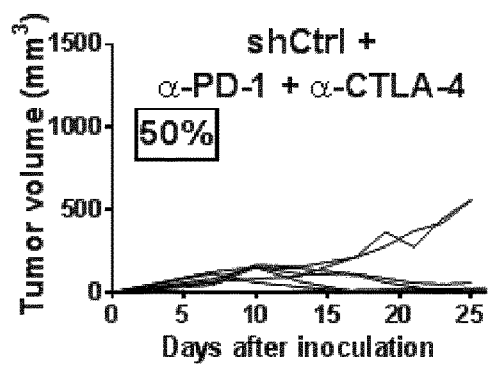
Figure 3B:
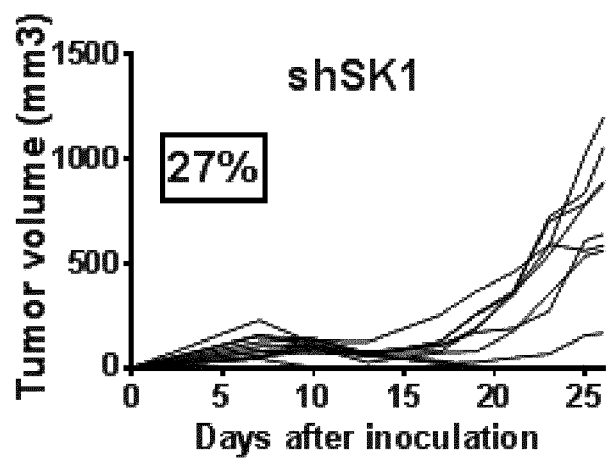
Figure 3B:
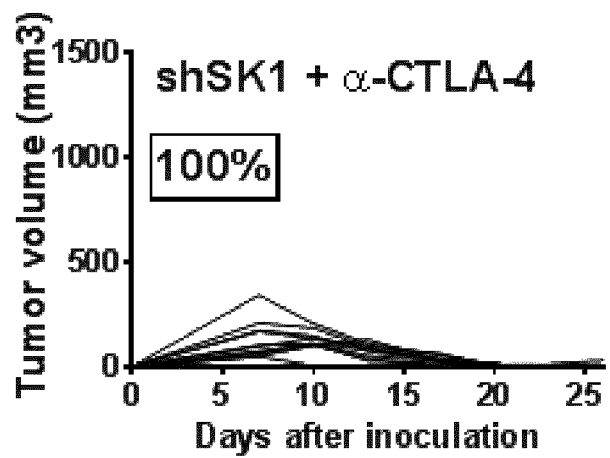
Figure 3B:
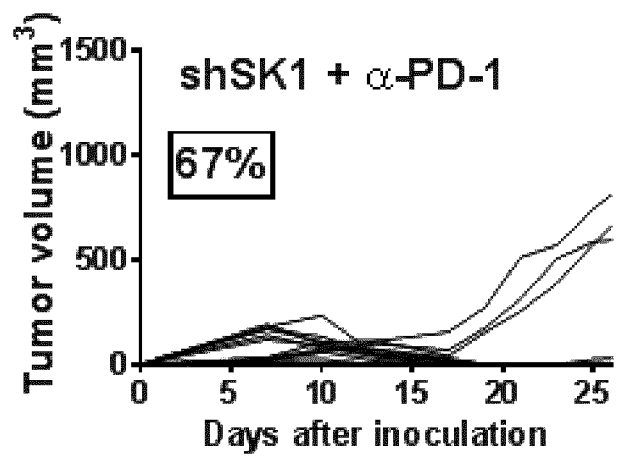

Given that SK1 downregulation was associated with an increase of tumor activated CD8+ T cells, we hypothesized that SK1 inhibition may improve the efficacy of Immune Checkpoint Inhibitors (ICI, e.g., anti-CTLA-4 and anti-PD-1). As shown in FIG. 3, whereas anti-CTLA-4 or/and anti-PD-1 treatment alone had limited effects on established Yumm tumors (FIG. 3A), SK1 silencing dramatically enhanced the response to anti-CTLA-4 or anti-PD-1 treatment, leading to tumor rejection in 100% and 67% of the animals, respectively (FIG. 3B). Moreover, SK1 downregulation significantly improved overall survival (FIG. 3C). Indeed, this combination (ICI+SK1 silencing) induced durable cures in 100% and 42% of the mice treated with anti-CTLA-4 and anti-PD-1, respectively, 2 months after cessation of therapy, suggesting the establishment of an effective immunological memory. Interestingly, amongst the long-term survivors, none of them developed a tumor upon a second melanoma cell injection, indicating that they were fully vaccinated against this melanoma cell line (data not shown). This enhanced response to ICI was associated with an increased CD8/Treg ratio in tumors (FIG. 3D). Of note, the CD8/Treg ratio is impressively increased in the tumors of Yumm ShSK1+anti-CTLA-4 group (Fold Change=16), this could explain the total tumor regression observed when using this combination.

Synergistic Anti-Cancer Immune Response of Immune Checkpoint Blockade and SK1 Pharmacological Inhibition.

To further confirm the potency of the combined therapy based on SK1 downregulation and ICI, we used SKI-I, a pharmacological inhibitor of SK1 (French, Schrecengost et al. 2003). Our data show that, whereas CTLA-4 blockade alone led to no tumor rejection at all, the combination of SKI-I+anti-CTLA-4 greatly synergized, resulting to total rejection in 67% of mice (FIG. 4A) and improved the overall survival (FIG. 4B). To confirm our observation with anti-PD-1, mice harboring Yumm tumors were treated with SKI-I combined or not with anti-PD-1. As shown in FIG. 5A, SKI-I enhanced the efficacy of anti-PD-1. Importantly, this effect was also observed in mice inoculated with MC38 colon carcinoma (FIG. 5B).

Collectively our data indicate that greater therapeutic success will be achieved by combining immune checkpoint blockade with agents that modulate the oncogenic SK1/S1P pathway. Interfering with sphingolipid metabolism may facilitate the development of novel avenues for therapeutic intervention in melanoma as well as in other cancer types.

REFERENCES

Throughout this application, various references describe the state of the art to which this invention pertains. The disclosures of these references are hereby incorporated by reference into the present disclosure.

Albinet, V., M. L. Bats, A. Huwiler, P. Rochaix, C. Chevreau, B. Segui, T. Levade and N. Andrieu-Abadie (2014). "Dual role of sphingosine kinase-1 in promoting the differentiation of dermal fibroblasts and the dissemination of melanoma cells." Oncogene 33(26): 3364-3373.

French, K. J., R. S. Schrecengost, B. D. Lee, Y. Zhuang, S. N. Smith, J. L. Eberly, J. K. Yun and C. D. Smith (2003). "Discovery and evaluation of inhibitors of human sphingosine kinase." Cancer Res 63(18): 5962-5969.

Lavieu, G., F. Scarlatti, G. Sala, S. Carpentier, T. Levade, R. Ghidoni, J. Botti and P. Codogno (2008). "Sphingolipids in macroautophagy." Methods Mol Biol 445: 159-173.

Pencheva, N., C. G. Buss, J. Posada, T. Merghoub and S. F. Tavazoie (2014). "Broad-spectrum therapeutic suppression of metastatic melanoma through nuclear hormone receptor activation." Cell 156(5): 986-1001.

The invention claimed is:

1. A method for enhancing the potency of an immune checkpoint inhibitor administered to a subject as part of a treatment regimen, the method comprising administering to the subject a pharmaceutically effective amount of a SK1 inhibitor in combination with the immune checkpoint inhibitor, wherein the immune checkpoint inhibitor is an antibody and wherein the SK1 inhibitor is a small molecule, and wherein the SK1 inhibitor is SK1-I.

2. A method of treating melanoma or colon cancer in a subject in need thereof comprising administering to the subject a therapeutically effective combination of an immune checkpoint inhibitor with a SK1 inhibitor, wherein administration of the combination results in enhanced therapeutic efficacy relative to the administration of the immune checkpoint inhibitor alone, wherein the immune checkpoint inhibitor is an antibody and wherein the SK1 inhibitor is a small molecule, and wherein the SK1 inhibitor is SK1-I and the immune checkpoint inhibitor is pembrolizumab.

3. The method of claim 1 wherein the subject suffers from a melanoma.

4. The method of claim 1 wherein the subject suffers from a melanoma resistant to BRAF inhibitors.

5. The method of claim 1 wherein the subject suffers from a melanoma with elevated plasma dehydrogenase (LDH).

6. The method of claim 1 wherein the subject suffers from a cancer characterized by a low tumor infiltration of CD8+ T cells.

7. The method of claim 1 wherein the immune checkpoint inhibitor is an antibody selected from the group consisting of anti-CTLA4 antibodies, anti-PD-1 antibodies, anti-PD-L1 antibodies, anti-PD-L2 antibodies anti-TIM-3 antibodies, anti-LAG3 antibodies, anti-B7H3 antibodies, anti-B7H4 antibodies, anti-BTLA antibodies, and anti-B7H6 antibodies.

* * * * *